United States Patent [19]
Freeman

[11] Patent Number: 5,958,760
[45] Date of Patent: Sep. 28, 1999

[54] SAMPLE PROCESSING DEVICE WITH A CHAMBER FORMING MEMBER

[75] Inventor: Thomas Charles Freeman, Cambridge, United Kingdom

[73] Assignee: Medical Research Council, London, United Kingdom

[21] Appl. No.: 08/930,491
[22] PCT Filed: Mar. 27, 1996
[86] PCT No.: PCT/GB96/00758
  § 371 Date: Feb. 4, 1998
  § 102(e) Date: Feb. 4, 1998
[87] PCT Pub. No.: WO96/30124
  PCT Pub. Date: Oct. 3, 1996

[30] Foreign Application Priority Data

Mar. 28, 1995 [GB] United Kingdom .................. 9506312

[51] Int. Cl.⁶ .................................................. C12M 1/34
[52] U.S. Cl. ................................. 435/286.5; 435/287.2; 435/288.3; 435/40.5; 422/68.1; 422/99; 422/104; 436/63; 436/174; 356/398
[58] Field of Search ...................... 435/286.5, 287.1, 435/287.2, 287.9, 288.3, 288.4, 288.5, 288.7, 303.1, 40.5, 40.51; 359/398; 422/102, 99, 68.1, 104; 356/246; 436/63, 174, 176

[56] References Cited

U.S. PATENT DOCUMENTS

| | | |
|---|---|---|
| 4,829,003 | 5/1989 | Arney, Jr. ............................... 435/287.1 |
| 5,192,503 | 3/1993 | McGrath et al. . |
| 5,281,516 | 1/1994 | Stapleton et al. . |
| 5,346,672 | 9/1994 | Stapleton et al. ....................... 435/288.3 |
| 5,364,790 | 11/1994 | Atwood et al. ......................... 435/288.3 |
| 5,460,945 | 10/1995 | Springer et al. ......................... 435/287.1 |

FOREIGN PATENT DOCUMENTS

| | | |
|---|---|---|
| 0 270 363 | 6/1988 | European Pat. Off. . |
| 310 399 | 4/1989 | European Pat. Off. . |
| 464 861 | 1/1992 | European Pat. Off. . |
| 2 234 348 | 1/1991 | United Kingdom . |
| 2 261 111 | 5/1993 | United Kingdom . |
| 89/00887 | 2/1989 | WIPO . |
| 91/07486 | 5/1991 | WIPO . |
| 93/19207 | 9/1993 | WIPO . |

*Primary Examiner*—William H. Beisner
*Attorney, Agent, or Firm*—Pillsbury, Madison & Sutro LLP

[57] ABSTRACT

Disclosed is a support retaining member (216) for use in processing a sample supported on a support (6), the member (216) being such than when assembled together with a support (6) it forms a support cell, the support cell comprising a substantially sealed chamber, the chamber being provided with a fluid inlet and a fluid outlet for the introduction and removal respectively of fluids used in processing the sample.

20 Claims, 16 Drawing Sheets

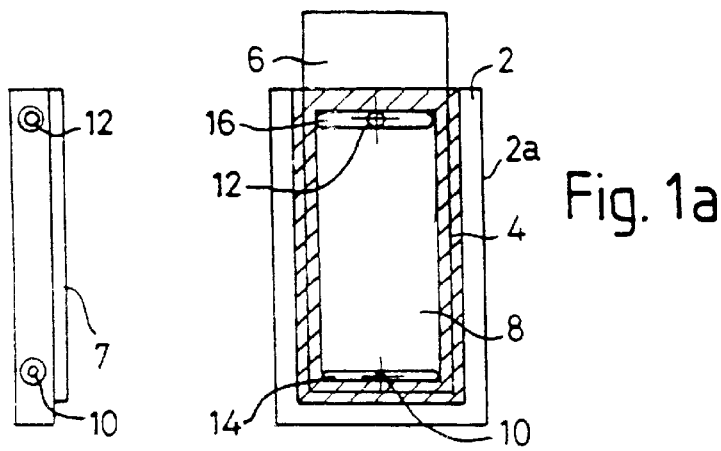
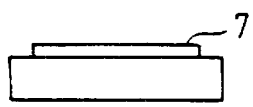
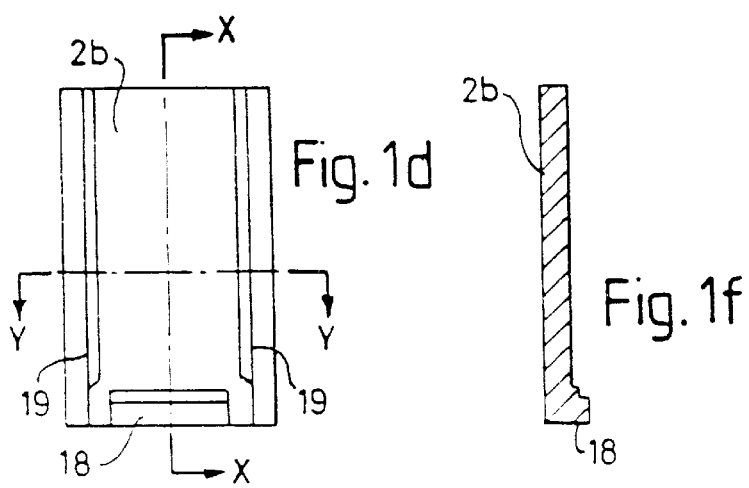
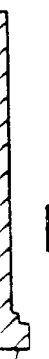
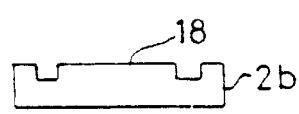
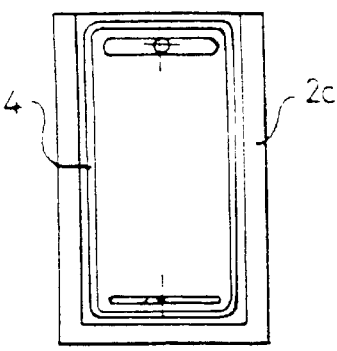

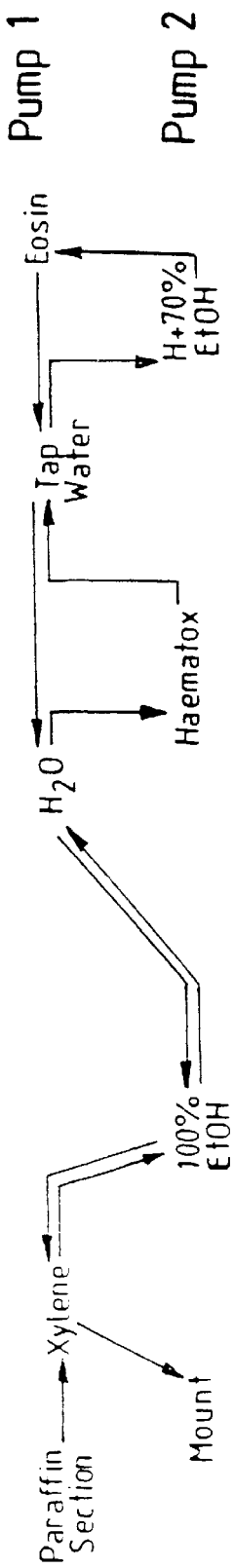

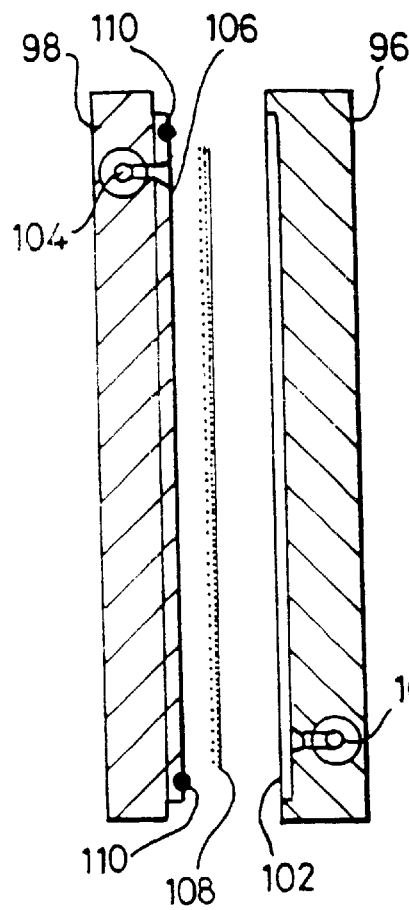
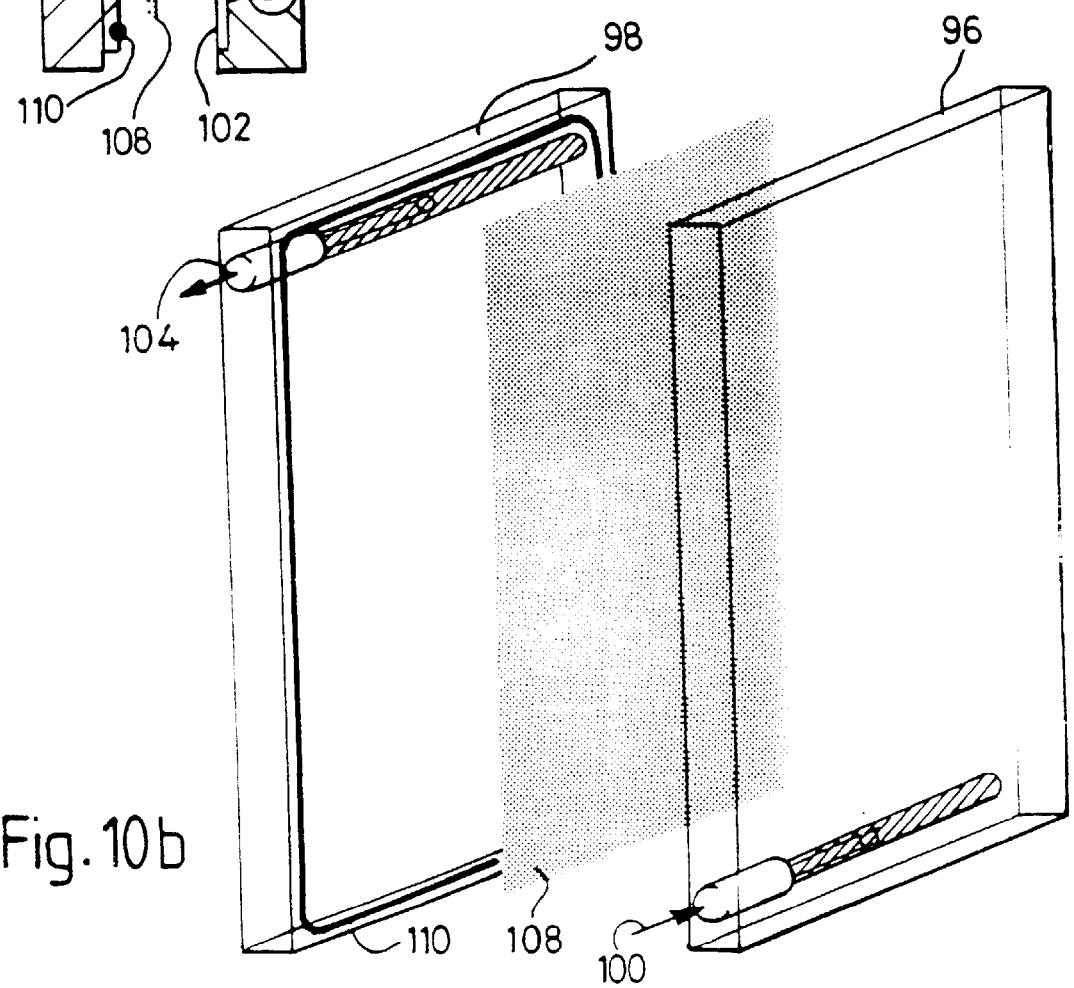
Fig. 10a
Fig. 10b

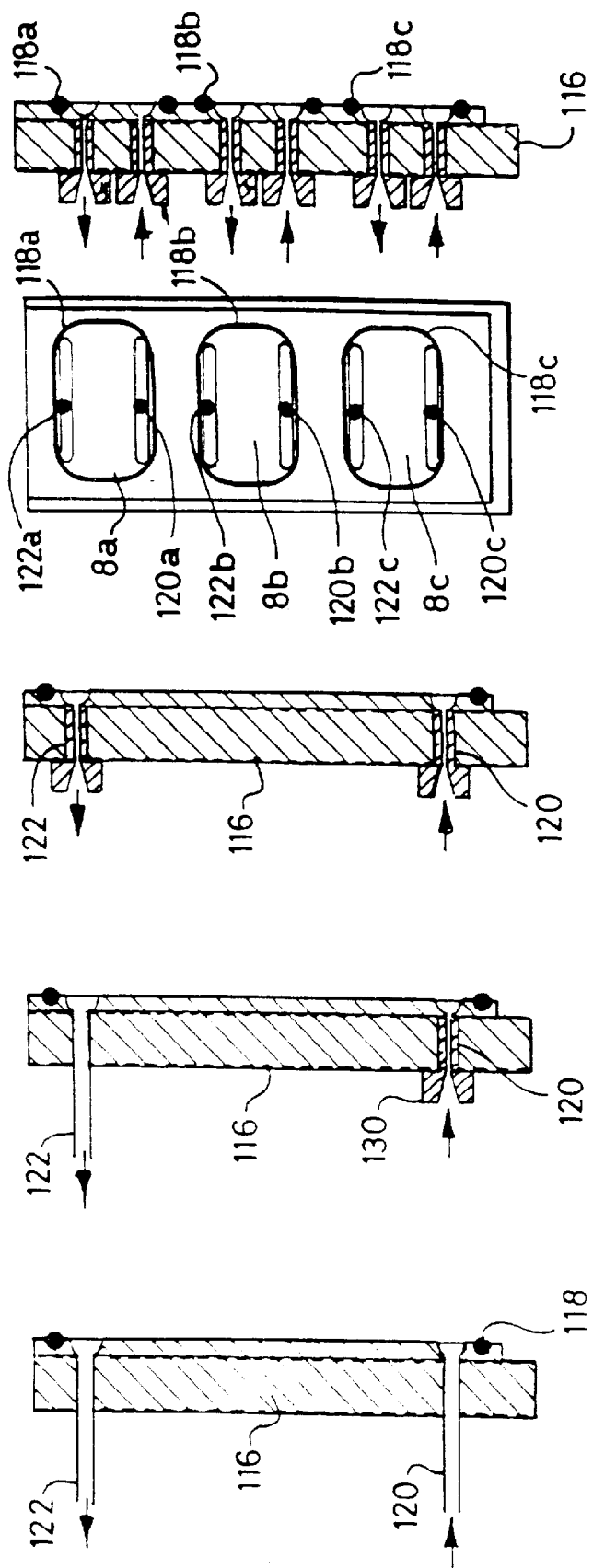

SAMPLE PROCESSING DEVICE WITH A CHAMBER FORMING MEMBER

This application is the national phase of international application PCT/GB96/00758, filed Mar. 27, 1996 which was designated the U.S.

FIELD OF THE INVENTION

This invention relates to a support cell for processing samples, particularly biological samples, supported on solid supports. In addition the invention relates to automated apparatus for processing samples supported on solid supports, which automated apparatus may be used with the support cell of the invention. The invention also relates to a method of processing a sample supported on a solid support.

BACKGROUND OF THE INVENTION

It is common practice, in certain technical fields, for samples of interest to be subjected to a particular process to be supported on solid supports. For example, protein or nucleic acid samples may be supported on filters or membranes: typically such filters or membranes are made of nylon or nitrocellulose. Samples, especially biological samples (e.g. cell suspensions or tissue sections) may also be supported on slides. Typically the slides are of transparent glass.

Samples supported on slides may be processed by a number of various techniques known to those skilled in the art, which include: standard staining techniques (e.g. Gram staining of micro-organisms, haemotoxylin/eosin staining of tissue sections); immuno- and enzyme cytochemistry (e.g. peroxidase/anti-peroxidase staining); ligand binding studies; in situ hybridisation of labelled DNA or RNA probes: and in situ amplification of nucleic acids present in a sample by means of polymerase chain reaction (PCR).

Typically, such processing is at present performed manually by laboratory personnel. This renders the processing slow and subject to individual variation (from one sample to the next, and/or from one day to the next), and is tedious for the personnel concerned. Some attempts have been made to provide apparatus to facilitate the immuno-cytochemistry process. Thus, for example, Shandon Scientific Limited manufacture the "Sequenza"™ and "Cadenza"® immunostaining apparatus. Use of the "Sequenza"™ apparatus involves attaching a coverplate to the slide to be processed, thereby forming a narrow channel between the slide and coverplate. The coverplate comprises a funnel-like open-ended portion which, when attached to a slide, forms an open-ended chamber, into which staining reagents are manually introduced. The reagent then flows, under the influence of gravity, into the channel between the slide and the attached coverplate. When a new reagent is introduced into the well it displaces the previous reagent into a waste collection tray at the bottom of the apparatus.

The "Cadenza"® apparatus utilises the same coverplate system but additionally provides programmable automated control means for applying reagents to the open-ended well of the assembled slide/coverplate.

In relation to processing of samples supported on membranes, such samples are commonly preparations of proteins (termed Western blots) or DNA (Southern blots) or RNA (Northern blots). The molecular species of interest is visualised on the supporting membrane using specific antibodies and an appropriate detection systems (in the case of Western blots) or by hybridisation with a labelled probe (in the case of Southern and Northern blots). These processing techniques currently require considerable manual processing of the membranes.

The prior art apparatus for processing samples on solid supports is therefore very simple and limited in the functions which it can perform. The present invention aims to provide apparatus capable of more general application.

SUMMARY OF THE INVENTION

In a first aspect the invention provides a support retaining member for use in processing a sample supported on a support, the member being such that when assembled together with a support it forms a support cell, the support cell comprising a substantially sealed chamber, the chamber being provided with a fluid inlet and a fluid outlet for the introduction and removal respectively of fluids used in processing the sample.

In a particular embodiment, part of the internal surface of the substantially sealed chamber is defined by the sample bearing surface of the support, which arrangement has the advantage of minimising the number of components involved.

Conveniently the support is a slide, or a membrane of the type known to those skilled in the art.

Where the support is a slide, the support retaining member will typically be of such dimensions that it may be used with slides of conventional size, (i.e. slides which typically are about 25.4 mm by 76.2 mm). Where the support is a membrane, the dimensions of the retaining member will similarly be of such dimensions that it may be used with membranes of conventional size (typically 80 mm by 120 mm), although membranes are rather more variable in size than slides.

In some embodiments the support retaining member comprises two opposed portions, the support being positioned between the opposed portions of the support retaining member when the support cell is assembled. Preferably at least that portion of the support retaining member which comes into contact with the fluids used to process the sample on the support is made of an inert material, such as a synthetic moulded plastics material. Perspex is found particularly suitable. The remainder of the support retaining member may generally be of the same or other material, e.g. glass, perspex or metal (such as duraluminium).

The components of the support cell are typically held together by clamping means. In certain embodiments the clamping means is capable of clamping together the portions of a plurality of support cells. Typically, from one to around twelve or sixteen support cells may be clamped simultaneously by a single clamping means. The support cells may preferably be arranged in the clamping means in a substantially horizontal or substantially vertical manner, although any position intermediate between these two positions may be possible. The support cells may, for example, be arranged side-by-side, or one in front of the other.

As an alternative, or in addition, to clamping means the support cell may be provided with biasing means, which biasing means tends to urge together the components of the support cell. Conveniently the biasing means will comprise one or more sprung biasing members. In a particular embodiment, the support retaining member is attached to clamping means by spring-loaded mounting pins, such that formation of the support cell places the springs of the spring-loaded mounting pins under compression, which springs therefore urge together the components of the support cell.

In preferred embodiments, the force applied to the support cell by the clamping means and/or the biasing means helps to ensure a fluid-tight seal between the support and the support retaining member.

It is generally preferred that the support cell additionally comprises sealing means to assist in the formation of the substantially sealed chamber. Conveniently the sealing means forms a fluid-tight seal, in the first instance with the sample bearing surface of the support and, in the second instance, with the support retaining member. Alternatively, the sealing means may effect a seal directly between opposed portions of the support retaining member, where the support retaining member is of two-part construction. The sealing means may be an integral part of the support retaining member, or may be provided as a separate component of the support cell. The sealing means typically comprises a gasket, which may be made of silicon rubber or other suitable material. In one embodiment the sealing means comprises an O-ring gasket, the shape of which is generally that of a frame-like surround seated in a groove in one portion of the support retaining member. In an alternative embodiment the sealing means comprises a flattened frame-like surround gasket (about 100 to 150 $\mu$m thick). Either type of gasket may be discarded after a single use (if, for example, contaminated with a radioactive probe) or may be re-used if desired. The flattened gasket embodiment is particularly suitable as a disposable gasket, to be discarded after a single use. It will be apparent that the thickness of the gasket (which can be readily altered by exchanging gaskets) may, in part, determine the volume of the substantially sealed chamber.

Conveniently the fluid inlet into, and the fluid outlet out of, the substantially sealed chamber are formed in the support retaining member. Where the support is a slide, the fluid inlet and fluid outlet are preferably provided in one portion where the support retaining member is of the two-part construction defined above. Where the support is a membrane, however, it is preferred that the fluid inlet and fluid outlet are provided in opposed portions of the support retaining member, where the support retaining member is of two-part construction. This encourages correct flow of processing fluids through the membrane.

The fluid inlet allows the introduction into the substantially sealed chamber of fluids needed to process the sample on the support. Typically such fluids will be buffers, solvents (e.g. ethanol/methanol, xylene), reagents (e.g. antibody- or probe-containing solutions) or stains. The fluid outlet allows for the processing fluids to be removed from the sample (e.g. for a washing step, or to allow the addition of a further reagent). Preferably, when the supports are being processed, their orientation is such that the fluid inlet is in the bottom portion of the substantially sealed chamber, and the fluid outlet is in the top portion of the substantially sealed chamber.

Typically, where the sample is supported on a slide, the substantially sealed chamber will have a volume of between 50 $\mu$l and 300 $\mu$l, preferably between 100–150 $\mu$l This small volume allows for economical use of reagents and (where temperature regulation is involved) a rapid thermal response time. Where the sample is supported on a membrane, the chamber will generally be larger (up to 2–3 mls).

In a particular embodiment, the support cell is adapted so as to be suitable for use in performing PCR on samples supported on a support (typically a slide), which hitherto has proved extremely difficult: performing PCR involves heating small volumes of liquids to comparatively high temperatures, which conventionally necessitates performing the PCR in a sealed reaction chamber to prevent undue evaporation loss of the reactants. However, the sealed chamber must be openable to allow the addition of further reagents. Such an openable chamber has hitherto been very difficult to create in the context of a standard slide. At present, the sealed chamber is typically created by placing a glass coverslip over a volume of PCR mix and sealing around the coverslip with a substance such as mineral oil or nail varnish. Re-opening the chamber is difficult and contamination of the chamber contents sometimes occurs. Also, the presence of the slide has hindered the ability rapidly to alter the temperature of the reagents, which ability is desirable when performing PCR.

In a particular embodiment envisaged for PCR (or other processes where temperature regulation is required), the support cell is equipped with temperature control means to allow for rapid heating and cooling of the sample and PCR mix (i.e. thermal cycling). Typically the support cell will be provided with an electrical heating element or a Peltier device. The support cell may also be adapted (e.g. by provision of cooling fins) to provide for improved air cooling. Temperature control in the range 4°–100° C. is found sufficient for most applications.

In a further aspect, the invention provides automated apparatus for processing a sample, especially a biological sample, supported on a support, the apparatus comprising: support holding means for holding one or more supports, the sample on the or each support being present within a respective substantially sealed chamber; fluid delivery means for delivering processing fluid to the or each chamber; waste fluid collecting means for removing fluid from the or each chamber; and computer control means.

Preferably the apparatus is used in conjunction with the support cell defined above. Conveniently the holding means comprises clamping means suitable for clamping together the components of the support cell, as defined previously. Conveniently the holding means can accommodate from ten to twenty-four support cells.

A number of arrangements for appropriate fluid delivery means can be envisaged. In a preferred embodiment a number of reservoirs (typically, 10) of processing fluids, (e.g. buffers, stains, etc.) are provided, each reservoir being attached to pump means. Preferred pump means are syringe pumps, such as those manufactured by Hook and Tucker, (Croydon, Surrey, UK), or Kloen having a stroke volume of between 1 and 10 ml. One such pump may be provided for each processing fluid reservoir, or a single pump may be provided to pump fluid from each a plurality of reservoirs, by means of a multi-port valve configuration.

Conveniently each syringe pump is in turn attached to a central manifold (such as a universal connector). Preferably the central manifold feeds into a selective multi-outlet valve such that, if desired, where a plurality of samples are being processed simultaneously, each sample may be treated with a different processing fluid or combination of processing fluids, such that samples can be individually processed. A suitable selective multi-outlet valve is a rotary valve, such as the 10 outlet rotary valve supplied by Omnifit (Cambridge, UK). Thus each outlet from the multi-outlet valve may be connected to a separate support cell. One or more filters (especially "on-line" filters) may be incorporated if desired. Typically a filter will be positioned between each reservoir and its associated syringe pump.

Each syringe pump may be actuated individually by the computer control means, or two or more pumps may be actuated simultaneously to provide a mixture of two or more processing fluids. Controlling the rate of operation of each pump will thus control the composition of the resulting mixture of processing fluids.

In an alternative embodiment, the fluid delivery means comprises two or more piston/HPLC-type pumps, each pump being supplied, via a multi-inlet valve, by a plurality of processing fluid reservoirs. Suitable pumps are available, for example, from Anachem (Luton, Beds, UK). Conveniently the multi-inlet valve will be a rotary valve. Each pump will feed into a rotary mixer, of the type well known to those skilled in the art, thus allowing variable composition mixtures of processing fluids to be produced, if desired.

Preferably, the processing fluid or mixture of processing fluids is then passed through an in-line filter and then conveniently passes through a selective multi-valve outlet (such as a rotary valve) before being fed into the support cells. Conveniently, each support cell inlet will be provided with a respective valve.

As an alternative to the generally "parallel" supply of processing fluids defined above, the processing fluids may be supplied in "series" such that, for example, fluid is passed from one substantially sealed chamber to another. This embodiment would be particularly suitable, for example, when applied to simple staining of samples and has the advantage that the amount of reagent required is minimised.

In general relation to the fluid delivery means, it is a further preferred feature that a multi-inlet valve be located close to the fluid inlet provided in the or each substantially sealed chamber. Typically the valve will be a three-way valve with two inlets, and one outlet leading to the substantially sealed chamber. One of the valve inlets is fed, indirectly, by the reservoirs of processing fluid. The second inlet is conveniently fed by a local reservoir which, typically, will be a syringe, pipette or micro-pipette (generally 100–5000 μl volume). This local reservoir may be controlled by the computer control means or may be manually controlled. The local reservoir will typically be used where a reagent is scarce (e.g. an antibody) or where the reagent is radioactive (e.g. a radio-labelled probe or ligand). The provision of such a local reservoir minimises the amount of reagent required, simplifies radioactive decontamination procedures, and provides extra flexibility in that each support cell may be processed individually, if required.

Preferably processing fluid will enter the or each respective substantially sealed chamber at the bottom, travel upwards and exit from the chamber via the fluid outlet at the top. The or each fluid outlet will conveniently empty into a common collecting duct, which duct drains into a collecting vessel. The vessel is desirably removable from the apparatus to allow for periodic emptying or decontamination.

In a preferred embodiment, the apparatus is also equipped with temperature control means, as many procedures require some or all of the steps to take place at a specific temperature (e.g. binding of antibodies, hybridisation of probes and primers or labelled ligands). These temperature dependent steps are generally performed between 4° C. and 95° C. for between 30 minutes and 24 hours. The temperature control means may be incorporated into the support cells (e.g. in the form of heating elements). Alternatively or additionally the support holding means may comprise, or be formed with, or be situated within, temperature control means. In a particular embodiment the support holding means is mounted on a block provided with a Peltier device temperature control means. Additionally, a fan may be provided to assist cooling of the apparatus.

The computer control means will generally comprise a personal computer (PC) or, more preferably, the computer control means will be integrated within the automated apparatus. Ideally, the computer control means should control two or more (preferably all) of the following parameters: the selection of which pump or pumps to actuate; the absolute volume and the rate of flow of processing fluid passing through the actuated pump(s); the selection of which support cell to feed with processing fluid; the temperature of the supported samples within the apparatus; and the timing of the various events.

It is envisaged that apparatus in accordance with the invention will be suitable for use, inter alia, in standard staining techniques, immuno- and enzyme cytochemistry (e.g. peroxidase/antiperoxidase staining); ligand binding studies; in situ hybridisation of labelled DNA or RNA probes; or even in situ PCR and in processing of Southern, Northern or Western blots. Preferably the computer control means has a programmable memory such that the steps needed to perform a certain procedure (e.g. haemotxylin/ eosin staining) can be entered into the computer memory and readily re-called without the need to re-program the computer.

Conveniently the apparatus may be substantially modular such that, should large numbers of supported samples require to be processed, further reservoirs, pumps, support cells etc., can be readily added to the existing equipment. In such an embodiment the apparatus is preferably capable of accepting a modular array of support cells, whether the samples are supported on slides or membranes.

The invention further relates to manufacture of and use of the support cell and/or the apparatus of the invention in processing a sample on a support, such that the invention provides: a method of processing a sample on a support using a support cell and/or the automated apparatus defined above: a method of making a support cell and a method of making automated apparatus in accordance with the invention.

The invention will now be further described by way of illustration and with reference to the accompanying drawings in which:

FIG. 1a is a plan view of a portion of a support retaining member (where the sample support is a glass slide);

FIGS. 1b and 1c being side and end elevations respectively of the portion illustrated in FIG. 1a;

FIG. 1d being a plan view of the portion of a support retaining member opposed to that shown in FIGS. 1a–1c;

FIG. 1e being an end elevation of the portion shown in FIG. 1d;

FIGS. 1f and 1g being respective sections along the lines XX and YY shown in FIG. 1d;

FIG. 2 is a plan view of a portion of a support retaining member, being a different embodiment to that shown in FIG. 1a;

FIGS. 7a and 7b are longitudinal sections through a support cell in accordance with the invention, together with a schematic representation of part of the associated fluid delivery means, the plane of the section in FIG. 7b being at 90° to the plane of the section in FIG. 7a;

FIG. 8a is a flow diagram illustrating schematically the steps performed in haemotoxylin/eosin staining of samples; and FIG. 8b shows how the same process could be performed using apparatus in accordance with the invention;

FIGS. 10a–10b are enlarged, exploded sectional and perspective views respectively of a support cell wherein the sample is immobilised on a membrane;

FIG. 11b is a sectional view of the same, along the dotted line Y—Y in FIG. 11a;

FIGS. 14a–14c show, in cross-section, sample retaining members suitable for use with particular embodiments of apparatus according to the invention;

FIG. 14d shows a plan view of a further sample retaining member; and

FIG. 14e is a cross-section of the member shown in FIG. 14d;

DETAILED DESCRIPTION OF EMBODIMENTS OF THE INVENTION

Figures 3A, 3B:
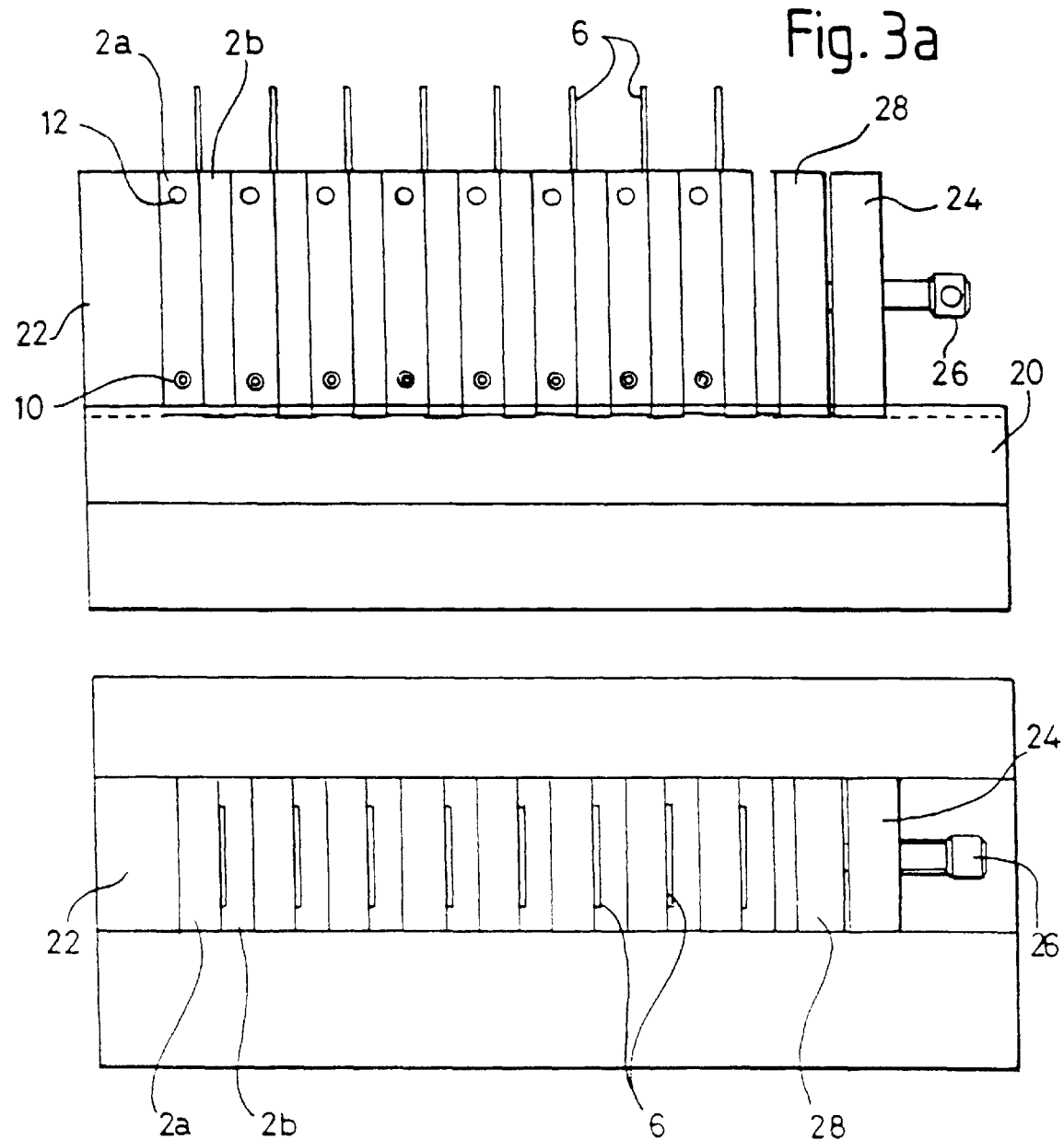
FIGS. 3a and 3b are side and plan elevations respectively of an array of support cells in accordance with the invention clamped within clamping means, which clamping means also forms part of support holding means in apparatus in accordance with the invention.

In the embodiment shown in FIGS. 1a–g, a support cell for use in processing a sample on a slide comprises a support retaining member 2 and sealing means 4, the support retaining member 2 being such that when assembled together with a support 6 and sealing means 4 it forms a support cell, the support cell comprising a substantially sealed chamber 8 the internal surface of which is defined in part of the sample bearing surface of the support 6, the chamber 8 being provided with a fluid inlet 10 and a fluid outlet 12 for the introduction and removal respectively of fluids used in processing the sample. The support 6 is a conventional glass slide.

The support retaining member 2 comprises two opposed portions, 2a and 2b, shown in plan view in FIGS. 1a and 1d respectively. The support 6 is positioned between the opposed portions 2a and 2b when the support cell is assembled.

Referring to FIG. 1a, one portion 2a of the support retaining member 2 is a generally rectangular block of perspex, about 37 mm wide, 7.5 mm thick and 60 mm long. In addition, the block is formed with a central raised region 7, 29 mm wide, 2.5 mm high and about 55 mm long. This central raised region is clearly shown in FIGS. 1b and 1c.

The sealing means 4 is a flattened silicon rubber gasket in the form of a frame-like surround, about 4 mm wide. The gasket 4 is of sufficient dimensions to extend around the fluid inlet 10 and the fluid outlet 12.

The fluid inlet 10 takes the form of a cylindrical bore, with a diameter of about 1 mm. The fluid inlet 10 enters the portion 2a of the support retaining 2 member at one side (as shown in FIG. 1b). The entrance to the fluid inlet 10 is formed with a cylindrical counter-bore about 10 mm deep and about 5.6 mm in diameter. The counter-bore facilitates the attachment of fluid delivery means. The cylindrical bore of the fluid inlet extends into the portion 2a about 20 mm and then passes through 90° to form an opening at one end of the central raised region of the portion 2a. The cylindrical bore of the fluid inlet 10 at this point widens into a long slot 14, extending across most of the width of the central raised region.

The other end of the central raised region has a larger slot 16 which narrows into the opening of the fluid outlet 12. The fluid outlet 12 is a cylindrical bore with a diameter of 2 mm (about twice the diameter of the fluid inlet 10), which passes through 90° to exit the portion 2a of the support retaining member at the same side as that on which the fluid inlet 10 enters the portion 2a (see FIG. 1b). The fluid outlet 12 is counter-bored in a similar manner to the fluid inlet 10 in order to facilitate attachment of waste fluid removal means.

As shown in FIG. 1d, the portion 2b of the support retaining member 2 is a generally rectangular block of duraluminium with overall dimensions similar to the portion 2a of the support retaining member 2. The portion 2b has stepped sides 19 and a stepped end region 18 at one end. FIG. 1e shows an end elevation of the portion 2b as seen from the end with the stepped end region 18 (the stepped sides are omitted for clarity). FIGS. 1f and 1g are sectional views along the lines XX and YY (in FIG. 1b) respectively. FIGS. 1a–1g are all drawn to the same scale.

In use, a support 6 (glass slide) bearing a sample to be processed is placed in the portion 2b of the support retaining member 2, the stepped sides 19 and stepped end region 18 serving to guide and retain the slide in the correct position. The support 6 is positioned such that the surface of the support 6 bearing the sample is furthermost from the portion 2b of the support retaining member 2.

The sealing means 4 (gasket) is then placed around the uppermost surface of the support 6, surrounding the sample to be processed. The positioning of the sealing means 4 is assisted by the stepped edges 19 and stepped end region 18 of the portion 2b of the support retaining member. The portion 2a of the support retaining member is then positioned on top of the sealing means 4, so as to make a substantially sealed chamber 8 largely defined by the surface of the support 6 bearing the sample and the opposed surface of the raised central region 7 of the portion 2a of the support retaining member 2. Again, positioning of the portion 2a is assisted by the stepped edges 19 and stepped end region 18 of the portion 2b. The apertures of the fluid inlet 10 and the fluid outlet 12 are within the substantially sealed chamber 8, the edges of which are defined by the sealing means 4.

The support cell assembly is then placed in a clamping means, ready for processing.

FIG. 2 shows a portion 2c of a support retaining member. The portion 2c is a generally rectangular perspex block substantially similar to the portion 2a shown in FIG. 1a. However, in the embodiment shown in FIG. 2, the sealing means 4 is a silicon rubber O-ring, which is seated in an accommodating groove cut in the raised central region of the portion 2c. The accommodating groove is about 1.5 mm wide and 0.88 mm deep. The mean corner radius of the turns in the groove at the four corners is about 3 mm.

FIG. 3a is a side elevation of clamping means 20 securing an array of eight support cells of the type shown in FIGS. 1 or 2. FIG. 3b shows a plan view of the same array. The clamping means 20 is generally rectangular and comprises a fixed end block 22, 24 at opposed ends, between which is provided a shallow channel (a few millimeters deep), of a width sufficient to accommodate a support cell array. The channel is slightly off-set from the medial axis of the clamping means. Fixed block 24 is formed with a screw-thread aperture, which aperture is in screw-threaded engagement with clamping screw 26. The outer end of clamping screw 26 is knurled to facilitate grip by an operator's fingers (but in an alternative embodiment a rod may be inserted through an aperture provided in the outer end of the clamping screw, perpendicular to the long axis thereof, which rod can be used to increase the turning moment applied to the screw). The inner end of clamping screw 26 is attached to a clamping face 28. Accordingly, turning clamping screw 26 moves the clamping face 28 towards or away from the fixed end block 22, such that between one and eight support cells may be secured in the clamping means 20 with a variable clamping force, which clamping force, in addition to securing the support cells also serves to ensure a good seal between the sealing means and the support/support retaining member.

The clamping means 20 is made of metal and has a perspex cover (not shown), which serves to prevent excessive heat loss of samples and is a safety feature when radioactive substances are used in the processing of the sample.

The clamping means 20 is about 225 mm long, 95 mm wide and 50 mm thick. The shallow channel is about 38 mm wide. However, where the samples on the supports are to be subjected to in situ PCR the overall dimensions of the clamping means will be reduced, thus decreasing its thermal capacity, allowing for quicker thermal cycling.

Typically the clamping means will be compatible with the automated apparatus of the invention and generally the clamping means will form at least part of the support holding means in the automated apparatus.

Figure 4:
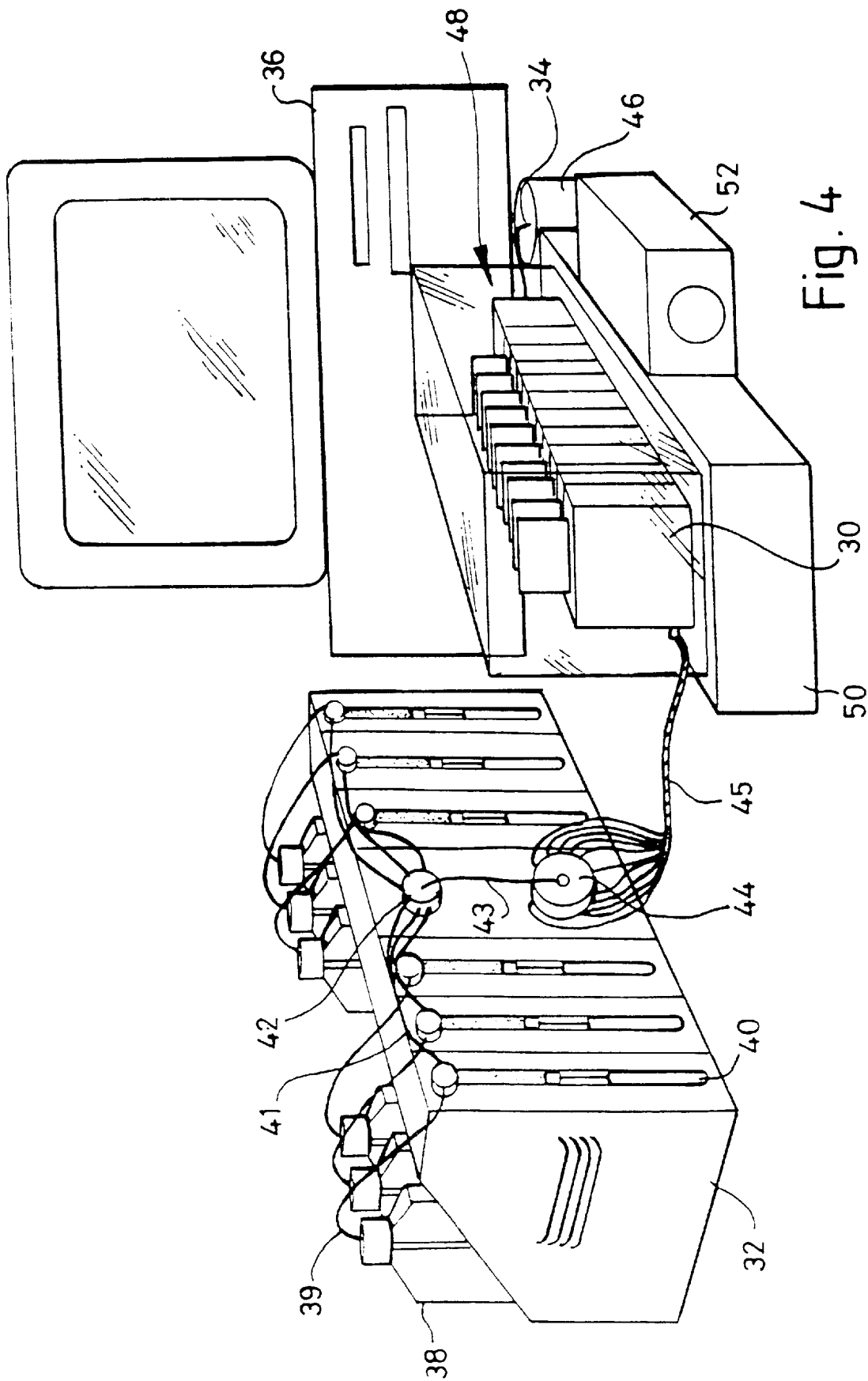
FIG. 4 shows a perspective view of apparatus in accordance with the invention.

FIG. 4 is a perspective view (to a different scale) of one embodiment of automated apparatus for processing a sample on a support in accordance with the invention. In FIG. 4, an array of ten support cells is held in a support holding means 30, which holding means comprises the clamping means 20 of FIG. 3. The sample on each support is present within an individual substantially sealed chamber, such as that indicated in FIG. 1a. The apparatus also comprises fluid delivery means (indicated generally at 32 in FIG. 4) for delivery processing fluid to each chamber, waste fluid collecting means 34 for removing fluid from each chamber, and computer control means 36.

More specifically, the fluid delivers means 32 comprises six reservoirs 38, each reservoir 38 containing about 1 liter of a processing fluid. Fluid is fed from each reservoir 38 through narrow synthetic plastics tubing 39 to an associated syringe pump 40. The syringe pumps are those supplied by Hook & Tucker (Croydon, Surrey, UK) and have a stroke volume of 1–10 mls. One syringe pump 40 is provided for each reservoir 38. Each syringe pump 40 feeds via a short length of tubing 41 into a universal connector 42 which is in turn connected via tubing 43 to an Omnifit rotary valve 44, provided with ten outlets. Each outlet from the rotary valve 44 is connected via tubing 45 to a fluid inlet in one of the support cells held in the holding means 30. Each of the fluid outlets is connected to a common waste fluid collecting means 34 which drains into a glass beaker 46.

The apparatus further comprises a perspex cover 48 located over the array of support cells. The support holding means 30 is located on a temperature control means 50, which takes the form of a fan-assisted Peltier device (fan omitted for clarity). A variable temperature regulation control 52 is provided. The computer control means is a PC which controls: the selection of which syringe pumps 40 to actuate; the absolute volume and the rate of flow of processing fluid; the selection of which support cell to feed with processing fluid; the temperature of the supported samples within the apparatus; and the timing of the various events.

Figure 5:
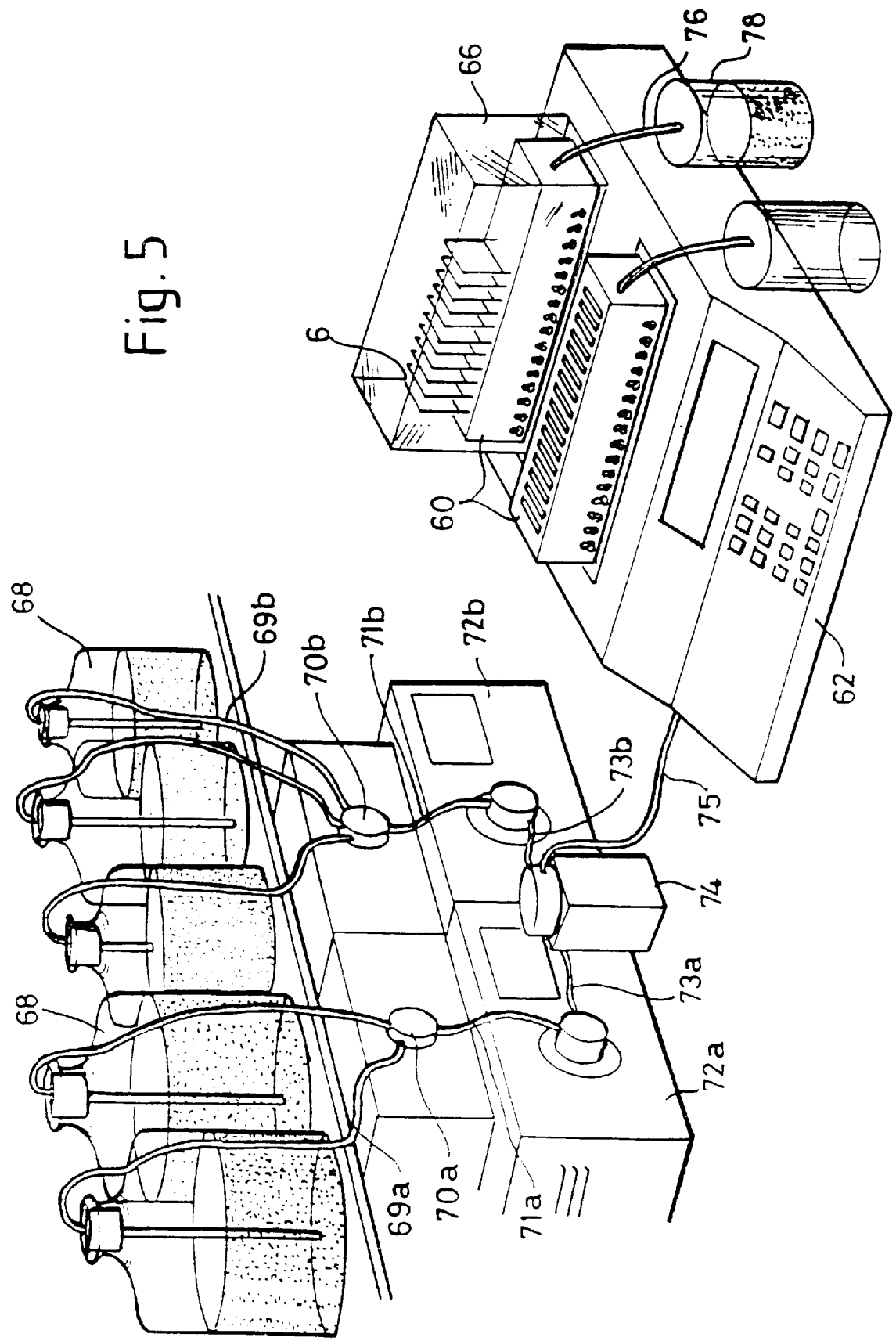
FIG. 5 shows a perspective view of a further embodiment of apparatus in accordance with the invention.

An alternative embodiment of the apparatus is shown (to a different scale) in FIG. 5. The embodiment shown in FIG. 5 comprises two support holding means 60, each of which is capable of supporting up to sixteen supports 6. The holding means 60 are mounted on a programmable thermal cycler 62. One of the holding means is occupied by eleven slides 6 and is covered with a perspex lid 66. Five reservoirs 68 of processing fluid are arranged on a shelf. Two reservoirs 68 are connected in a synthetic plastics tubing 69a to rotary valve 70a whilst the other three are connected via tubing 69b to rotary valve 70b. Rotary valve 70a is in turn connected via tubing 71 a to HPLC pump 72a, whilst rotary valve 70b is connected through tubing 71b to HPLC pump 72b. The HPLC pumps 72a, 72b each feed through tubing 73a,b into mixer unit 74, thus allowing variable composition mixtures of processing fluids to be produced, if desired. The processing fluid(s) passes through tubing 75 and then enters each chamber in the array of support cells and waste fluid exhausted therefrom is collected by a common waste duct 76, which empties into a glass collecing beaker 78.

Figure 6:
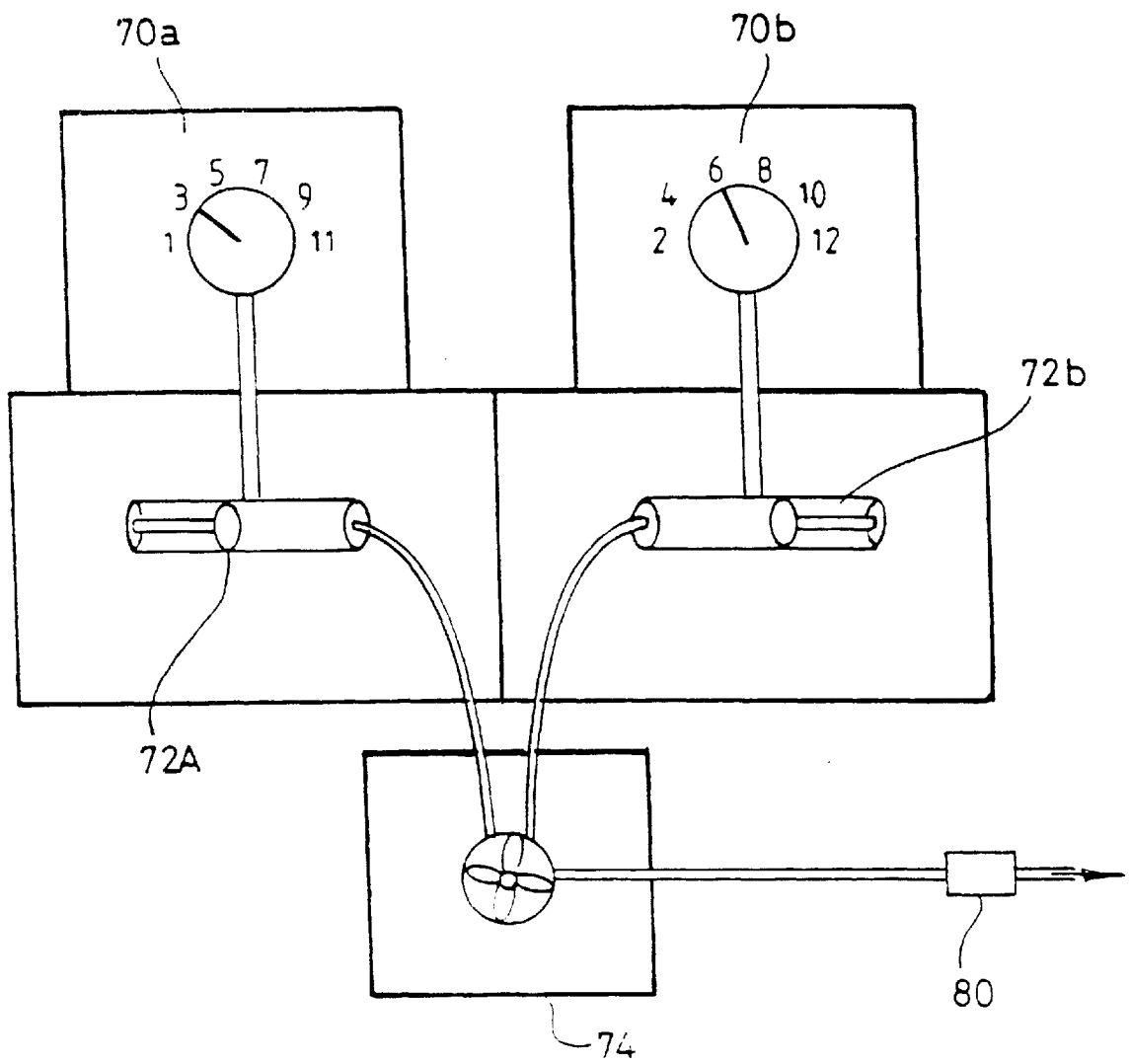
FIG. 6 is a schematic representation of part of the fluid delivery means for use in one embodiment of the apparatus of the invention.

The arrangement of the fluid delivery apparatus in this embodiment is shown schematically in FIG. 6. In FIG. 6, a filter unit 80 is included downstream of the mixer unit 74.

Figure 7A:
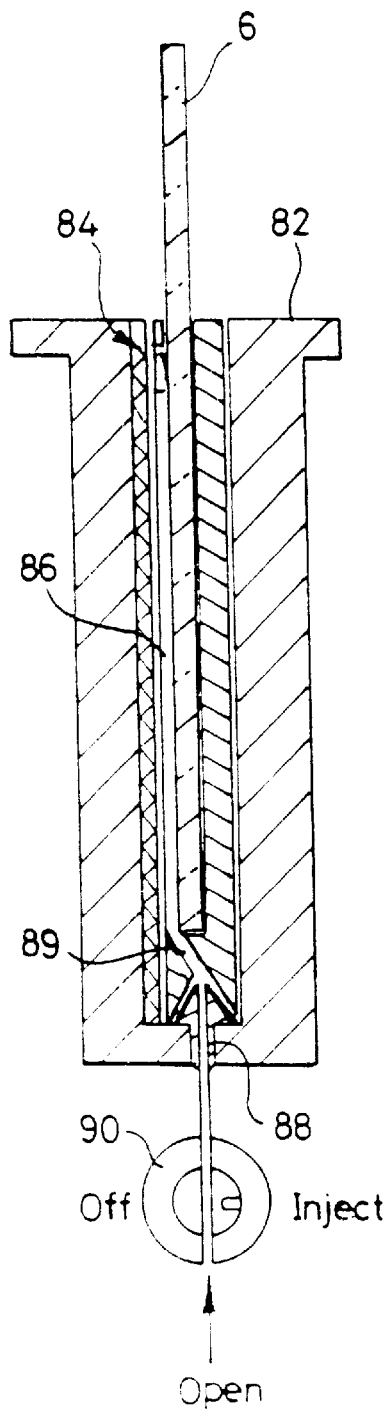

In the embodiment of a support cell shown in FIG. 7a, a support retaining member 82 accommodates a support 6 (glass slide) and an electrical heating element 84. A substantially sealed chamber 86 is defined by the surface of the support 6 upon which the sample is located and the opposed surface of the support retaining member 82, the seal being effected by a silicon rubber gasket (not shown). A fluid inlet is provided at the bottom of the chamber 86, which fluid inlet is attached to a three-way valve 90.

Figure 7B:
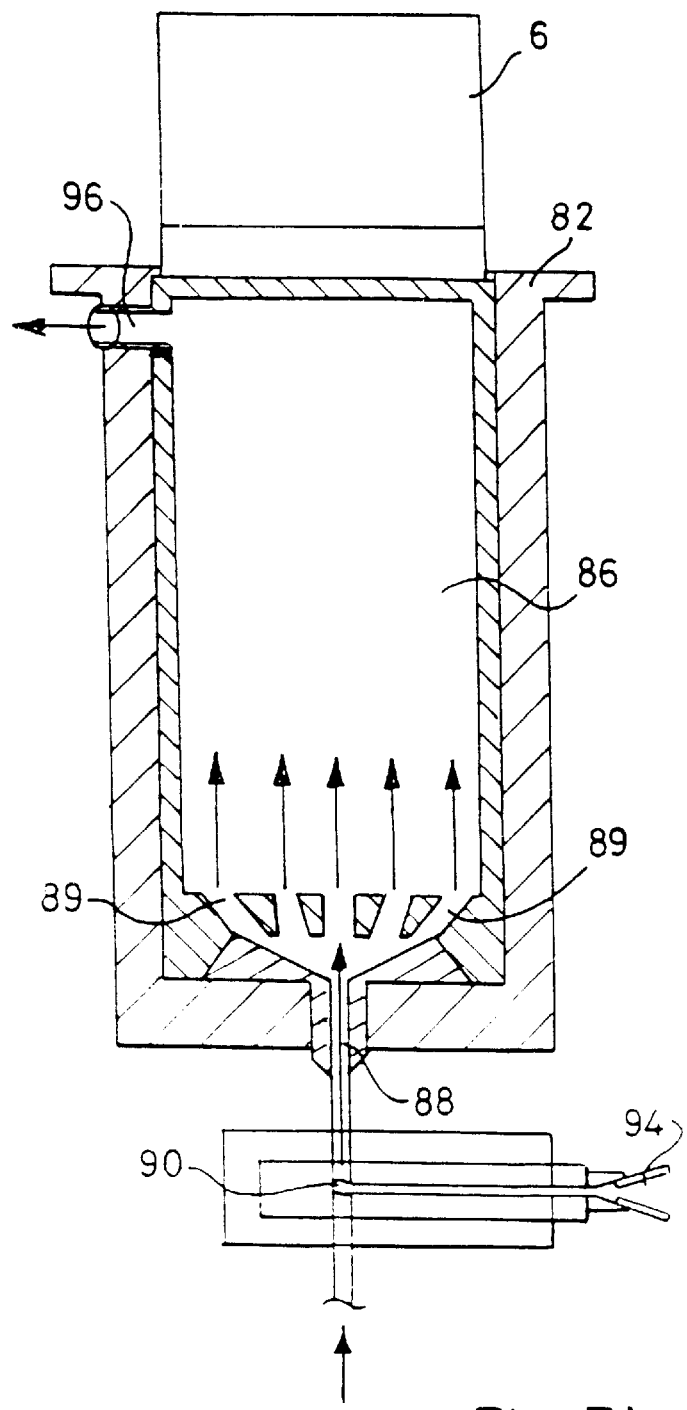

In FIG. 7b, the main feed from the reservoirs of processing fluid is indicated at 92 and is attached to one of the ports of the three-way valve 90. In addition, a syringe 94 forms a local reservoir which is connected to a second of the ports of the three-way valve 90. The local reservoir 94 will typically be utilised where the processing of the sample involves the use of scarce and/or radioactive reagents. The fluid inlet 88 splits into a number of channels 89, such that processing fluids will enter the substantially sealed chamber 86 along a broad front and advance upwards evenly before exiting the chamber 86 via outlet 96, thence into the common waste collecting duct (not shown).

FIG. 8a shows the flow diagram for performing haematoxylin/eosin staining of biological samples.

FIG. 8b shows how the process could be performed using automated apparatus in accordance with the invention, the fluid delivery means comprising two HPLC-type pumps.

Figure 9A:
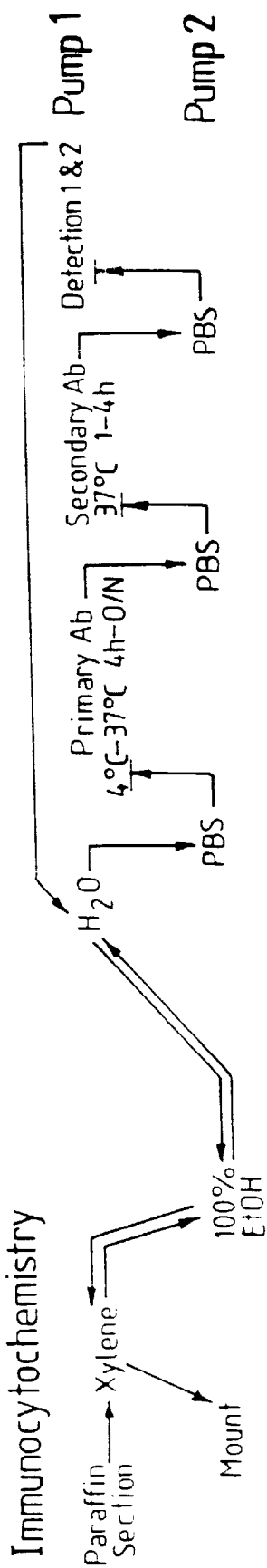
FIGS. 9a–9c are flow diagrams illustrating schematically how apparatus in accordance with the invention could be used to perform immunocytochemistry processing, in situ hybridisation and in situ PCR respectively.
Figure 9B:
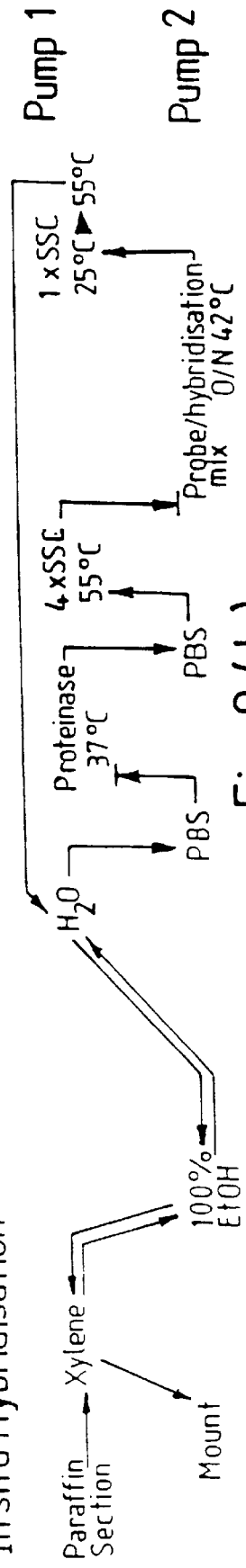
Figure 9C:
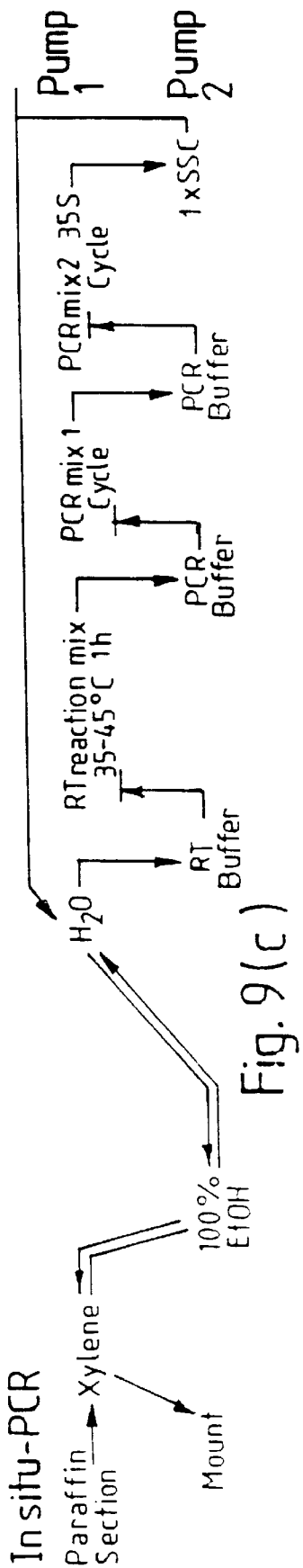

Similarly, FIGS. 9a–9c are flow diagrams showing how apparatus in accordance with the invention, utilising an HPLC-type two pump system, could be employed to perform an immunocytochemical process (9a), in situ hybridisation (9b) or in situ PCR (9c). Tables I and II indicate, respectively, sample protocols for performing haematoxylin/eosin staining and in situ hybridisation of a paraffin-treated thin section, using a six-syringe pump system.

In the embodiment shown in FIGS. 10a and 10b a support cell comprises two opposed portions 96, 98 of a support retaining member. The portion 96 is equipped with a fluid inlet 100 and a recessed area 102. The portion 98 is formed with a fluid outlet 104 and a raised section 106. The dimensions of the recessed section 102 of the portion 96 are such as to accept the raised section 106 of the portion 98, with a membrane sample support 108 positioned therebetween.

The raised section 106 is provided with a peripheral groove, which groove accommodates an O ring silicon rubber gasket 110.

When the support cell is assembled, a substantially sealed chamber is defined by the O ring gasket 110 and the opposed portions 96, 98 of the support retaining member.

Figure 11A:
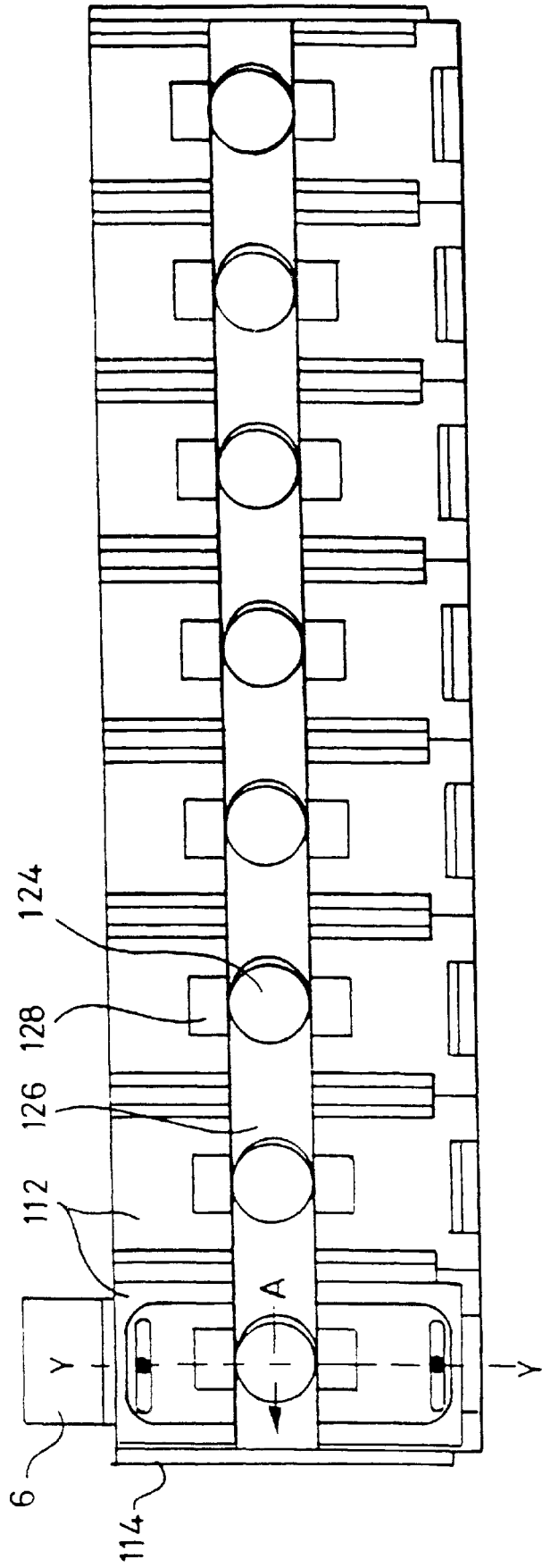
FIG. 11a is side elevation (to a different scale) of apparatus in accordance with the invention.
Figure 11B:
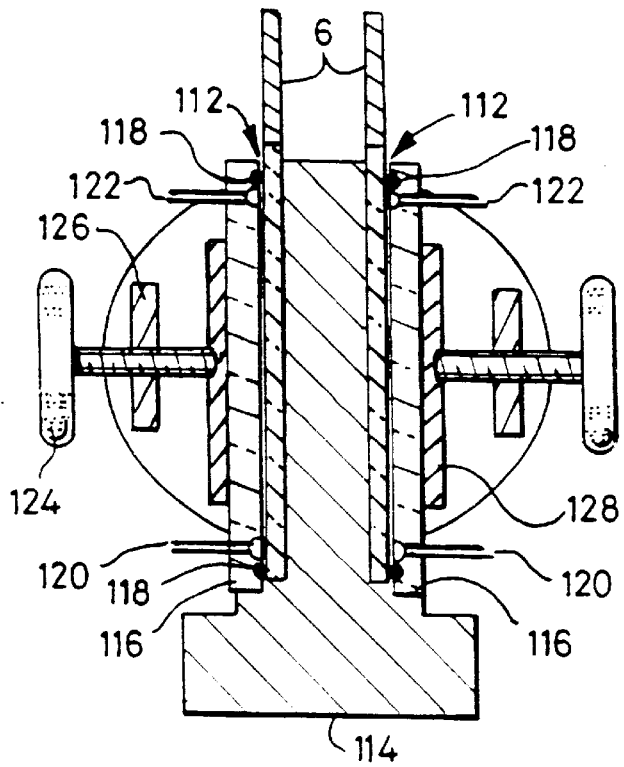

A further embodiment is illustrated in FIGS. 11a–11b.

In FIG. 11a a substantially vertical array of 16 support cells 112 is provided, eight support cells 112 being disposed on either side of a central support holding member 114. The sample supports 6 are omitted (for clarity) from the support cells 112 except from that on the left hand end.

The arrangement is more clearly shown in the sectional view of FIG. 11b. The sample supports 6 (glass slides) are held on a shelf on either side of the support holding member 114. Each support cell comprises a sample support 6 and a perspex support retaining member 116. The support retaining members 116 are seated on a shelf either side of the support holding member 114, which comprises duraluminium, a good thermal conductor. Each support retaining member 116 is similar to the portion 2a of the support retaining member shown in FIGS. 1a–1c. Each section of the support holding member 114 which holds a sample support 6 is similar to the portion 2b of the support retaining member shown in FIGS. 1d–1g. A substantially sealed chamber is defined by the sample bearing surface of the support 6, the opposed surface of the support retaining member 116 and by an O ring gasket sealing means 118. Each substantially sealed chamber is provided with a fluid inlet 120 near the bottom of the support cell, and with a fluid outlet 122 near the top of the support cell. The fluid inlet 120 and outlet 122 are thus provided in a single support retaining member 116. The support cells 112 are clamped in place on the support holding member 114 by clamping means. The clamping means comprises, for each support cell 112, a screw threaded clamping member 124, which is in screw threaded engagement with an engagement bar 126 which runs the length of the apparatus and is supported at each end. The outer end of the clamping member 124 is provided with a knurled knob to facilitate manual operation. The opposite end of the clamping member 124 is provided with, or contacts, a clamping plate 128. Clamping plate 128 serves to spread the clamping force of the clamping member 124 over a greater area of the support retaining member 116.

Figure 12:
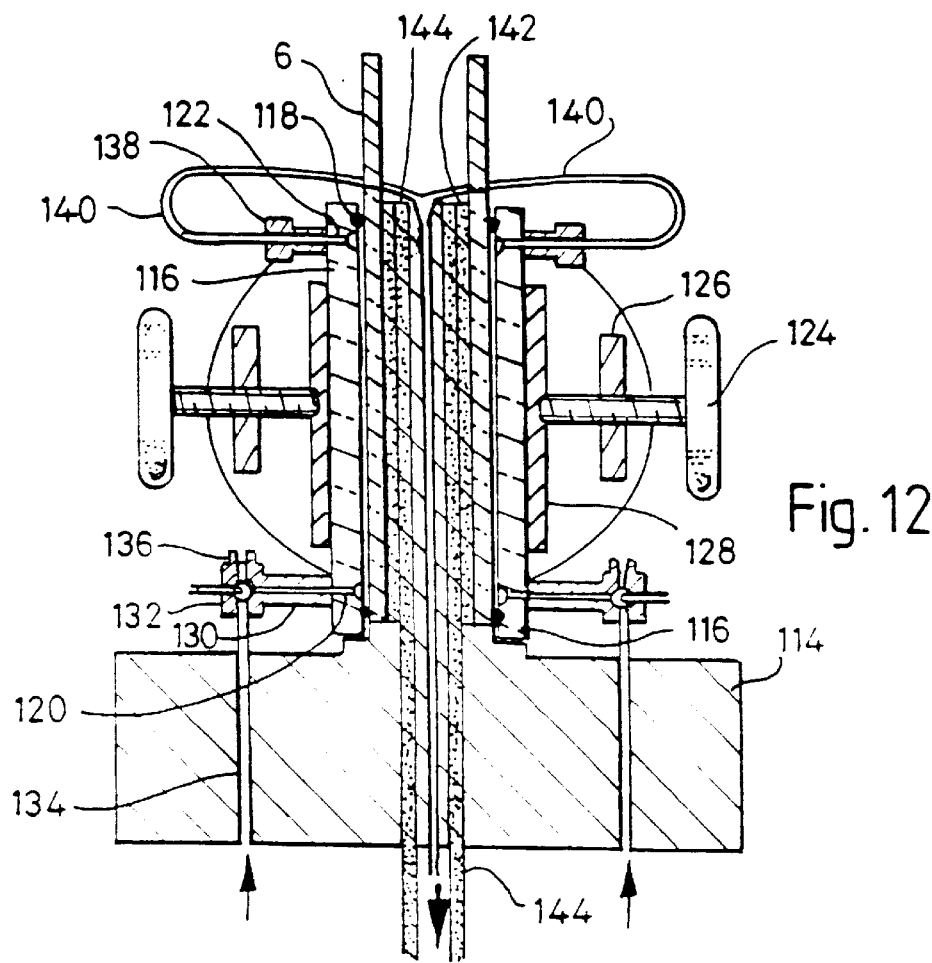
FIG. 12 shows, on a different scale, a sectional view of apparatus in accordance with the invention, similar to that shown in FIG. 11, adapted for performing processing of samples requiring careful temperature regulation (e.g. in situ PCR)

FIG. 12 is a sectional view of similar apparatus in an embodiment adapted to perform processing steps requiring careful temperature regulation, in particular, thermal cycling such as is necessary to perform in situ PCR. The arrangement is similar to that shown in FIG. 11b with each support cell comprising a sample support 6 and a perspex support retaining member 116. A substantially sealed chamber is defined by the sample bearing surface of the support 6, the opposed surface of the support retaining member 116 and by an O ring gasket sealing means 118. As previously, the support cells are clamped on either side of the support holding member 114 by clamping members 124 provided with clamping plates 128, the clamping members 124 being in screw-threaded engagement with an engagement bar 126.

The fluid inlet 120 is equipped with a Luer fitting 130, to which is attached a three-way valve 132. The valve 132 allows introduction of processing fluid from remote fluid delivery means via duct 134 which passes through the base of the holding member 114, or introduction of fluid from a local reservoir via short duct 136, which is adapted to receive a micropipette tip. In addition, duct 136 may be sealed at its outer end by a cap (omitted for clarity) or by covering with mineral oil.

The fluid outlet 122 is similarly provided with a luer fitting 138, allowing for ready attachment of waste fluid collecting tubing 140, which passes through the centre of the holding member 114, for convenience.

The support holding member 114 is formed with a plurality of integral heating elements 142 which come into direct contact with the sample supports 6. The heating elements 142 are metallic and electrically powered. The support holding member 114 is also provided with cooling means, which comprises a series of conducting vessels 144 which pass in close proximity to the sample supports 6. The conducting vessels 144 are adapted to receive a rapid flow of a fluid coolant (such as water), which is forced through the conducting vessels by a pump. The cooling system may be "closed" (with continuous re-cycling of coolant) or "open" (in which coolant passes out of the system after completing one circuit, and is replenished with fresh coolant).

Figure 13A:
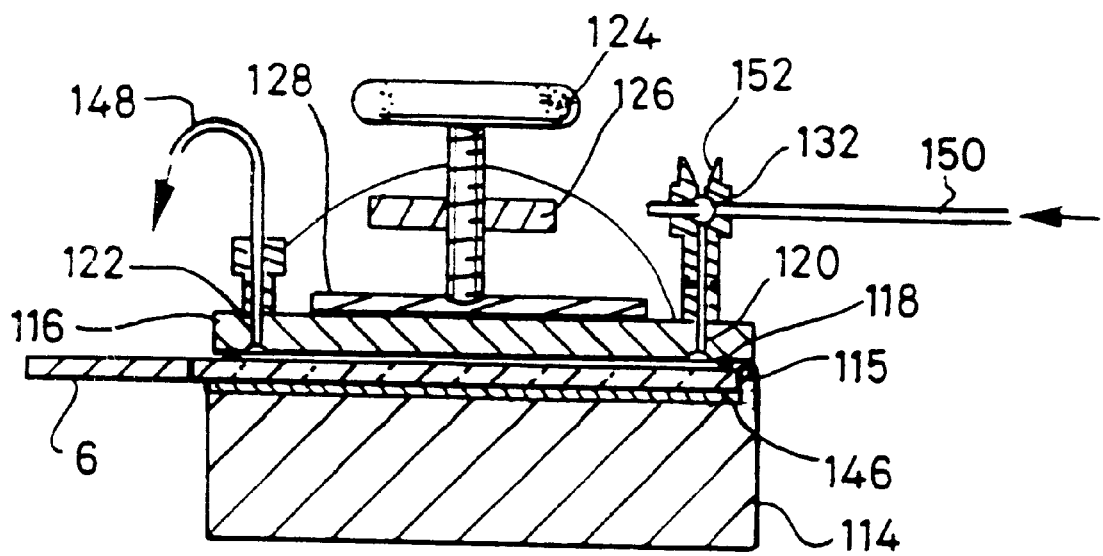
FIGS. 13a and 13b show in cross-section apparatus in accordance with the invention wherein sample supports are positioned substantially horizontally.
Figure 13B:
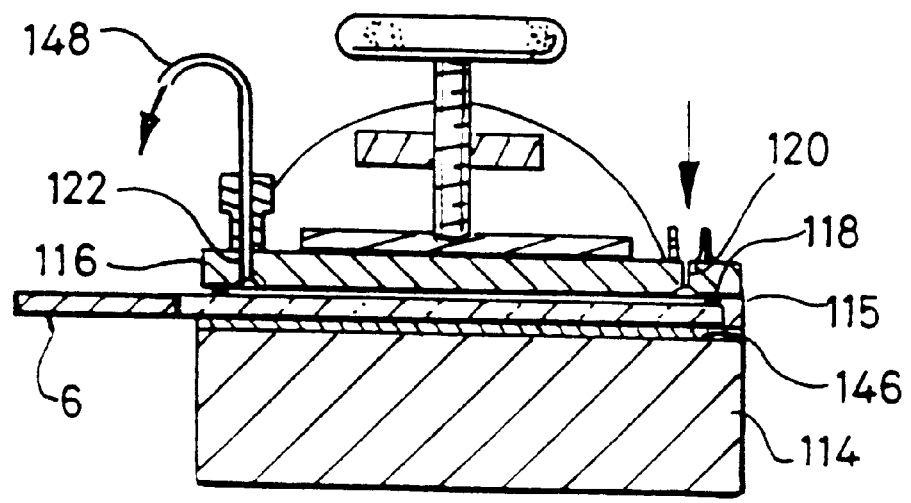

FIGS. 13a and 13b illustrate an embodiment of apparatus in accordance with the invention, wherein the support cells are positioned substantially horizontally. As with the embodiments illustrated in FIGS. 11 and 12, an array of support cells is positioned on a support holding member 114, each support cell comprising a substantially sealed chamber defined by the sample bearing surface of a support 6, the opposed surface of a support retaining member 116 and by an O ring gasket sealing means 118. Positioning of the support 6 and the support retaining member 116 on the support holding member 114 is assisted by a stepped edge 115 provided on the holding member 114.

The support cells are clamped in position on the holding member 114 by clamping means comprising a clamping member 124 formed with a clamping plate 128, the clamping member 124 being in screw threaded engagement with an engaging member 126.

The holding member 114 is provided with a temperature regulation Peltier device 146 which is in direct contact with the sample support 6 and provides for the heating and cooling thereof. In the embodiment shown in FIG. 13a, the fluid outlet 122 is equipped with a luer fitting for the convenient attachment of a waste fluid collecting tubing 148, whilst the processing fluid inlet 120 is provided with a luer fitting to which is attached a three way valve 132. The valve 132 allows for the introduction of processing fluid from a remote fluid delivery means (via duct 150) or from a local reservoir, by the insertion of a micropipette tip into duct 152. The duct 152 may be sealed by a synthetic plastics cap (not shown) or by the introduction of mineral oil. The arrangement shown in FIG. 13b differs in that the fluid inlet 120 is adapted to receive processing fluid directly from a micropipette tip.

It will be apparent that the holding member 114 in this embodiment could readily be altered by substituting the Peltier device 146 with separate heating and cooling means, as provided in the embodiment shown in FIG. 12.

FIG. 14 shows a number of various configurations that might be used for the slide retaining member 116 for use with any of the apparatus embodiments shown in FIGS. 11–13. FIG. 14a shows the basic arrangement, with a fluid inlet 120 provided near the bottom of the member 116 is positioned vertically) and a fluid outlet 122 provided near the top. The member 116 has a stepped profile on its inner face, to assist in position relative to a sample support and/or a support holding member. The member 116 is also provided with an O ring gasket sealing means 118, seated in a peripheral groove. In the embodiment shown in 14b, the fluid inlet 120 is formed with a luer fitting 130, to facilitate the attachment of associated fluid delivery means such as tubing or valves. In the embodiment shown in FIG. 14c, both the fluid inlet 120 and the fluid outlet 122 are formed with luer fittings.

The arrangement shown in 14d is slightly more complex in that, when assembled together with an appropriate sample support (e.g. glass slide), the support retaining member is capable of simultaneously forming three substantially sealed chambers 8a, 8b and 8c, each of which is provided with a respective fluid inlet 120a,b,c and a respective fluid outlet 122a,b,c, the sides of the substantially sealed chamber being sealed by respective O rings 118a,b,c.

Figures 15A, 15B:
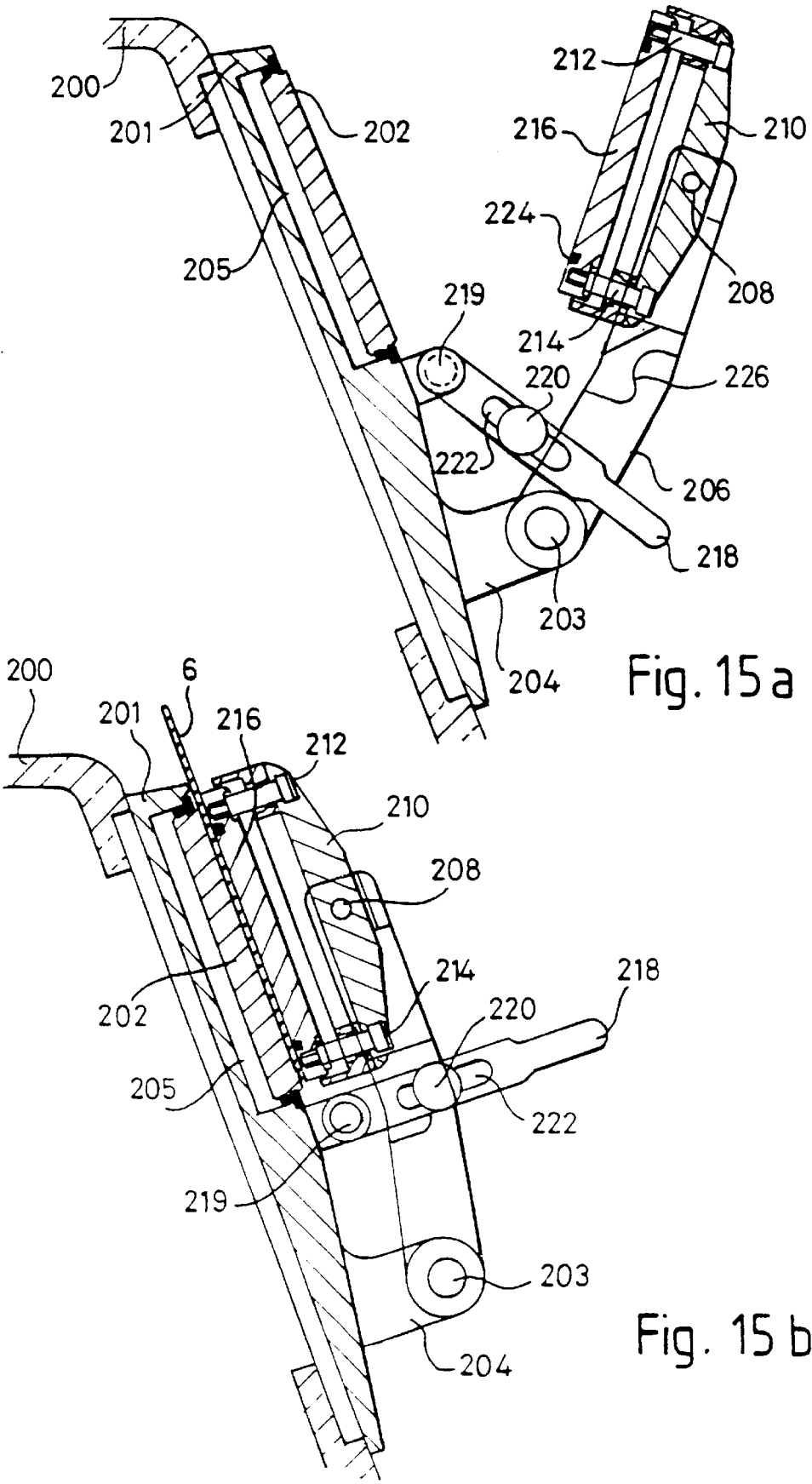
FIGS. 15a and 15b are side elevations (partly in sectional view) of apparatus in accordance with the invention, in an open, disassembled position (15a) and in a closed, assembled position (15b)

FIGS. 15a, b illustrate a preferred embodiment of apparatus in accordance with the invention, as shown in side elevation (partly in sectional view). FIG. 15a shows the apparatus in an open position, whilst FIG. 15b shows the apparatus in a closed, operational position.

Referring to FIG. 15a, the apparatus comprises a perspex housing 200, accommodating a detachable aluminium fitting 201. Four such fittings 201 are provided on the apparatus, although only one is shown, the rest being omitted for clarity. The fitting 201 detaches from the housing 200 to facilitate cleaning, maintenance and the like. Each fitting 201 is formed with six, metallic support holding members 202. Each support holding member 202 is retained in the fitting 201 by a silicone rubber gasket in such a way that an air-filled space 205 is formed between the support holding members 202 and the fitting 201. Each support holding member 202 is equipped with electrical heating means. The insulation afforded by the air-filled space 205 allows for rapid temperature regulation of the support holding members 202 by their respective electrical heating means, and thus rapid temperature regulation of supports held on the support holding members 202. Each support holding means 202 is also provided with temperature sensing means (not shown).

Twelve projections 204 are provided on the fitting 201, one pair of projections 204 being located beneath each support holding member 202. A pair of angled arms 206 is pivotally mounted at one end region on a pivot 203 provided in each pair of projections 204. At the opposed end region of the angled arms 206 is provided a pivotal attachment 208, upon which is mounted a pivoting head-piece 210. The head-piece 210 is provided with an upper and lower spring-loaded mounting pin 212, 214, which pins 212, 214 are engaged with a support retaining member 216.

There are thus six support retaining members 216 associated with each of the four fittings 201 provided on the apparatus. Each support retaining member 216 is of substantially similar construction to the portion labelled 2a of the support retaining member shown in FIGS. 1a–1c. The support retaining member 216 is formed in perspex with a fluid inlet and a fluid outlet (not shown in FIG. 15, but labelled as 228 and 230 respectively in FIG. 16).

The arrangement is such that the pair of angled arms 206 may be moved about pivot 203 in a vertical plane from an open position, as shown in FIG. 15a, to a closed, operational position as shown in FIG. 15b, and vice versa. Movement of the angled arms 206 upwards towards the housing 200, brings the support retaining member 216 into close proximity, in the closed position, with the support holding member 202. Movement of the angled arms 206 may be effected manually, by the operator of the apparatus.

The apparatus may be retained in the closed position by actuation of a clamping means, which comprises a metallic, generally cylindrical, clamping lever 218 provided between each pair of angled arms 206 and pivotally mounted, at one end region, to a pivot 219 provided on the housing 200 above the projection 204. Within the clamping lever 218 is a transverse member 220. The transverse member 220 protrudes on each side beyond the surface of the clamping lever 218, and has limited degree of travel within the lever 218 defined by the slot 222 provided in the lever 218. The transverse member 220 is mounted on a spring (not shown), located between the transverse member 220 and the end region of the lever 218 opposed to that end region of the lever 218 mounted on the pivot 219.

In use, a sample support (microscope slide, 6) is positioned in a machined recess (not shown) provided on the sample support holding member 202, the sample bearing surface facing outwards, away from the support holding member 202. The angled arms 206 (and thus, the head-piece 210, and the support retaining member 216) are moved into the closed position by the operator, as shown in FIG. 15b. In the closed position a support cell is formed, comprising a substantially sealed chamber defined by the sample bearing surface of the sample support 6, the support retaining member 216, and the O ring gasket 224 provided in a machined recess formed in the surface of the support retaining member 216. A good seal between the gasket 224 and the sample-bearing surface of the sample support 6 is ensured by the spring-loaded mounting pins 212, 214, which bias the support retaining member 216 towards the support holding member 202 and the support 6.

Once in the closed position, the arrangement is clamped by the clamping lever 218. To effect clamping the lever 218 is moved upwards about the pivot 203. The transverse member 220 engages a co-operating recess 226 in the angled arms 206, such that the upward movement of the clamping lever 218 forces the transverse member to move within the slot 222 away from the pivot 219, against the spring located within the lever 218, causing the spring to become compressed. The compression of the spring provides the clamping force which clamps the arrangement in the closed position.

When the sample has been processed, the clamping lever 218 may be moved downwards about the pivot 219, disengaging the transverse member 220 from the co-operating recess 226. The support retaining member 216 may then be moved away from the support holding member 202, and the support 6 removed from the apparatus. If further samples are to be processed, the procedure may then be repeated.

Figure 16:
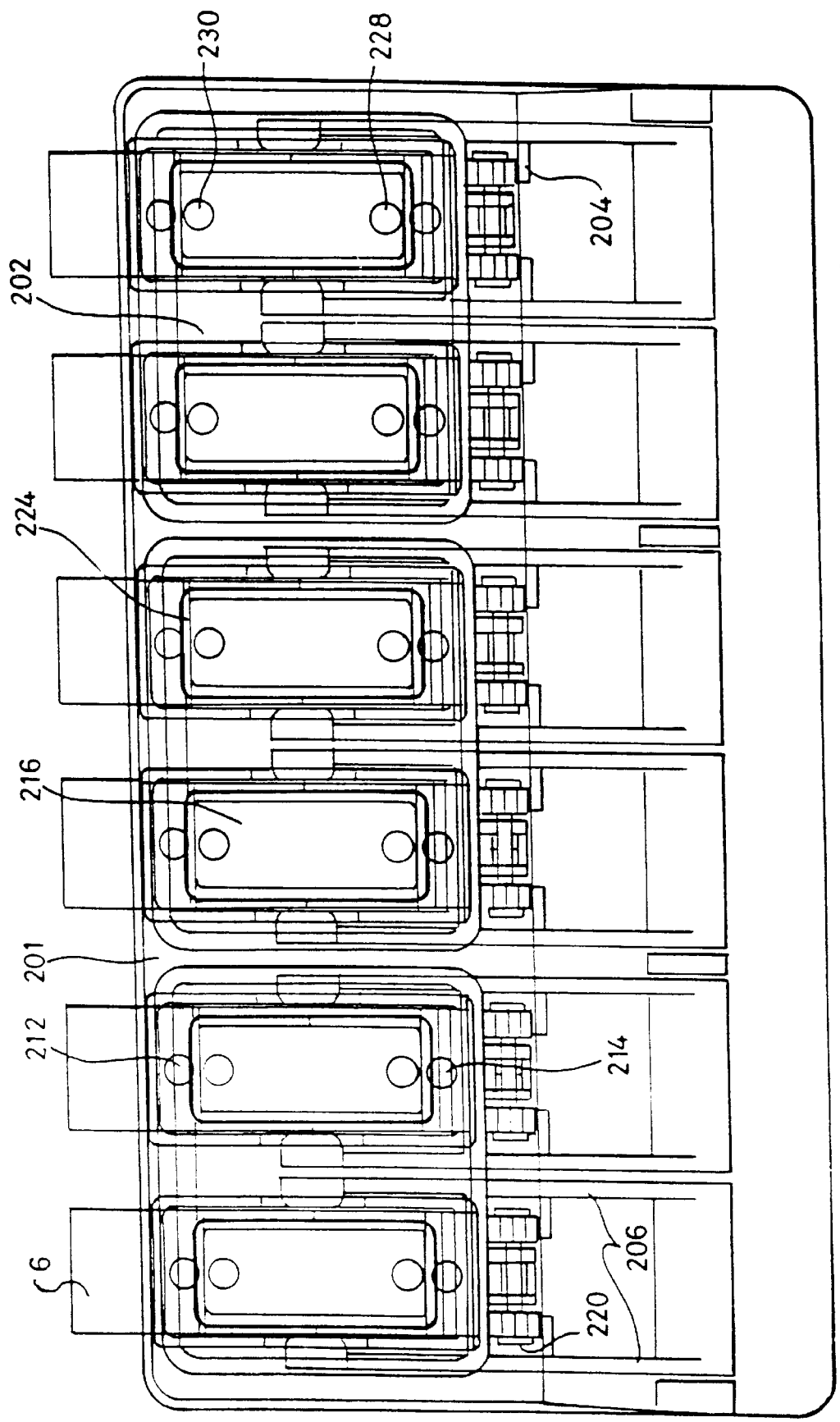
FIG. 16 is a front elevation of an array of six support cells of the type shown in FIG. 15, in their assembled position.

FIG. 16 illustrates an array of six support cells of the type shown in FIG. 15. The support cells are arranged in three pairs, each pair being associated with a respective support holding member 202, such that one thermoregulatable plate comprised in the support holding member 202 may regulate the temperature of two sample supports 6. Each support cell is provided with a fluid inlet 228 and a fluid outlet 230 formed in the support retaining members 216.

The support retaining members 216 are provided with round-bottomed grooves where the inlet 228 and outlet 230 enter the support cell, which grooves allow for even distribution of fluid across the width of the sample support as fluid enters the support cell, and which facilitate egress of the fluid via outlet 230. The apparatus comprises fluid delivery means, including ten reservoirs of fluids accommodated within the housing 200. Capillary tubing conducts fluids from the reservoirs, through apertures in the housing and through bores in the support retaining members 216 to the support cell inlets 228. Waste fluid egresses from the outlets 230, through bores in the support retaining members 216 and thence via capillary tubing through apertures in the housing 200 to a waste fluid collecting vessel. Conveniently the capillary tubing is attached to, or located within, the angled arms 206, making for a tidier arrangement with less chance of the tubing becoming snagged.

In a preferred embodiment, the automated apparatus for processing samples comprises four arrays of support holding members of the type shown in FIG. 16, such that the apparatus may process up to 24 samples simultaneously. The arrangement illustrated in FIG. 16 has the advantage that an operator may observe the processing fluids within the support cells (the support retaining members 216 comprising perspex) and thus easily monitor the progress of the sample processing.

Figure 17:
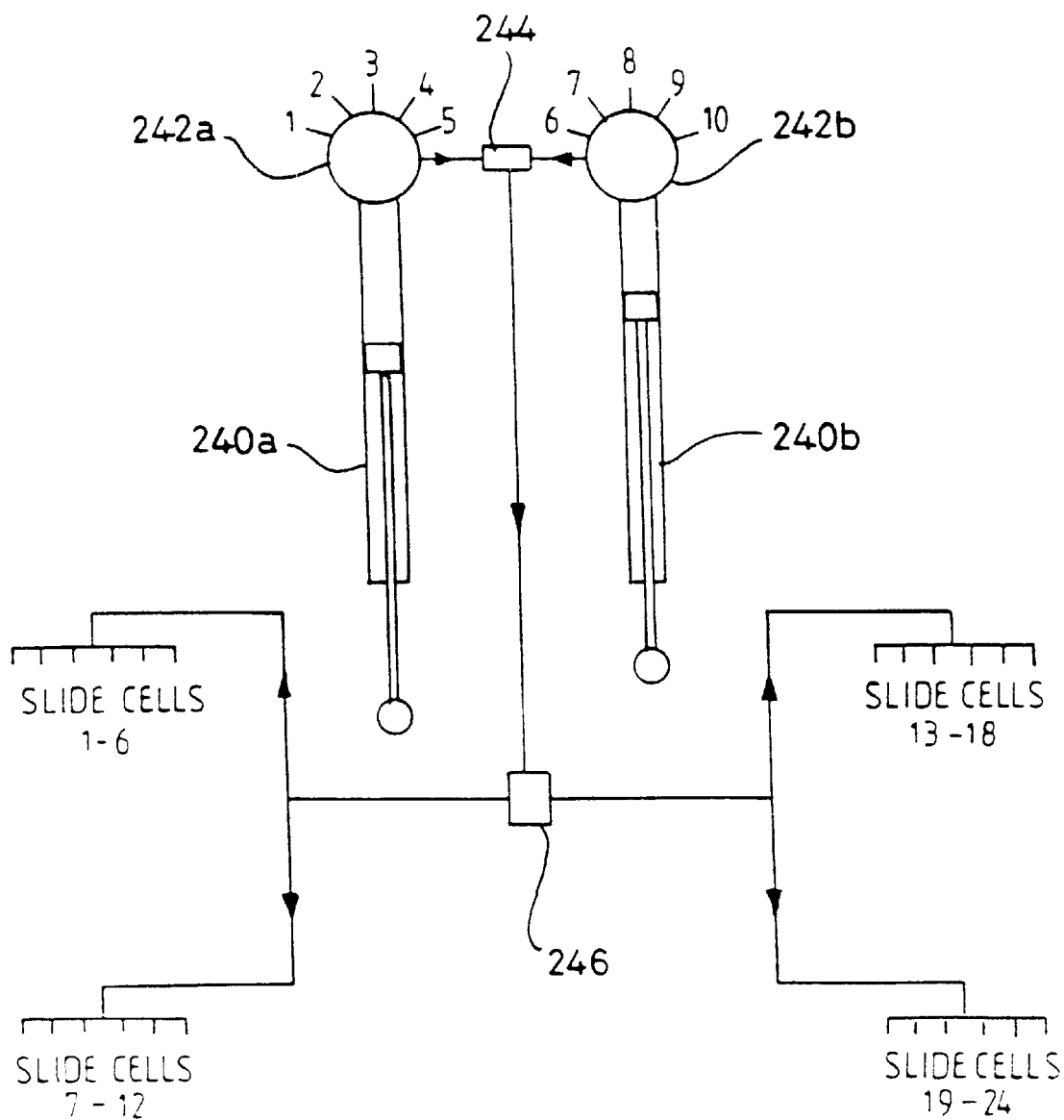
FIG. 17 is a schematic representation of fluid delivery means for use with apparatus in accordance with the invention.

The preferred embodiment of the automated apparatus is provided with fluid delivers means of the type illustrated schematically in FIG. 17. The fluid delivers means comprises two Kloen syringe pumps 240a, b fitted with 1 ml syringes. At the top of each syringe is located a 6-port rotary valve 242a, b, each rotary valve 242a, b being provided with 5 inlet ports and 1 exit port. Thus syringe pump 240a may pump fluid selected from one of five different fluid reservoirs 1–5, and syringe pump 240b may pump fluid selected from one of five different fluid reservoirs 6–10, each reservoir being connected to the syringe pumps 240a, b by a respective port in the rotary valves 242a, b. The syringe pumps 240a, b force fluid via the exit ports of the rotary valves 242a, b into a common mixing valve 244, thence to a distribution valve 246, which directs the fluid to the appropriate array of support cells. Each support cell is provided with a 3-way valve, such that respective support cells may be processed individually with different processing fluids if desired, and allowing for the manual introduction of processing fluids into individual support cells (e.g. by means of a micropipette).

Tables I and II describe example protocols for performing haematoxylin/eosin staining and in situ hybridisation respectively using automated apparatus according to the invention.

It will be clear that other embodiments of the invention could be made and such variants are intended to fall within the scope of the present invention.

TABLE I

Haematoxylin and Eosin Stain
Example Protocol for Slide Processor

| Stage | Pump No. | Soln. | Ratio | Vol (µl) | Rate (ml/mm) | Cells | Pause (sec) | Repeat | Temp. (° C.) |
|---|---|---|---|---|---|---|---|---|---|
| 1 | 1 | EtOH | — | 1000 | 2 | 1–6 | 60 | 2 | 22 |
| 2 | 1 & 2 | EtOH/H$_2$O | 9:1 | 1000 | 2 | 1–6 | 60 | 1 | 22 |
| 3 | 1 & 2 | EtOH/H$_2$O | 7:3 | 1000 | 2 | 1–6 | 60 | 1 | 22 |
| 4 | 1 & 2 | EtOH/H$_2$O | 1:1 | 1000 | 2 | 1–6 | 60 | 1 | 22 |
| 5 | 2 | H$_2$O | — | 1000 | 2 | 1–6 | — | 10 | 22 |
| 6 | 3 | Haem. | — | 800 | 2 | 1–6 | 300 | 1 | 22 |
| 7 | 2 | H$_2$O | — | 1000 | 2 | 1–6 | 10 | 10 | 22 |
| 8 | 4 | H+EtOH | — | 1000 | 2 | 1–6 | 30 | 3 | 22 |
| 9 | 2 | H$_2$O | — | 1000 | 2 | 1–6 | — | 10 | 22 |
| 10 | 5 | Eosin | — | 1000 | 2 | 1–6 | 120 | 1 | 22 |
| 11 | 2 | H$_2$O | — | 1000 | 2 | 1–6 | — | 15 | 22 |
| 12 | 1 & 2 | EtOH/H$_2$O | 1:1 | 1000 | 2 | 1–6 | 60 | 1 | 22 |
| 13 | 1 & 2 | EtOH/H$_2$O | 7:3 | 1000 | 2 | 1–6 | 60 | 1 | 22 |
| 14 | 1 & 2 | EtOH/H$_2$O | 9:1 | 1000 | 2 | 1–6 | 60 | 2 | 22 |
| 15 | 1 | EtOH | — | 1000 | 2 | 1–6 | 60 | 4 | 22 |
| 16 | 6 | Xylene | — | 100 | 2 | 1–6 | 30 | 4 | 22 |

TABLE II

In Situ Hybridisation from Paraffin Section
Example Protocol for Slide Processor

| Stage | Pump No. | Soln. | Ratio | Vol (µl) | Rate (ml/mm) | Cells | Pause | Repeat | Temp. (° C.) |
|---|---|---|---|---|---|---|---|---|---|
| 1 | 1 | Xylene | — | 1000 | 2 | 1–8 | 00:60 | 4 | 37 |
| 2 | 1 | EtOH | — | 1000 | 2 | 1–8 | 00:60 | 2 | 22 |
| 3 | 2 & 3 | EtOH/H$_2$O | 9:1 | 1000 | 2 | 1–8 | 00:60 | 1 | 22 |
| 4 | 2 & 3 | EtOH/H$_2$O | 7:3 | 1000 | 2 | 1–8 | 00:60 | 1 | 22 |
| 5 | 2 & 3 | EtOH/H$_2$O | 1:1 | 1000 | 2 | 1–8 | 00:60 | 1 | 22 |
| 6 | 3 | H$_2$O | — | 1000 | 2 | 1–8 | — | 10 | 22 |
| 7 | 4 | PreHyb.Buffer | — | 300 | 2 | 1–8 | 60:00 | 1 | 42 |
| 8 | Hold | Manual add. probe | | | | | 360:00 | | 42 |
| 9 | 5 | 1 × SSC | — | 1000 | 2 | 1–8 | 30 | 5 | 22 |
| 10 | 5 | 1 × SSC | — | 1000 | 2 | 1–8 | 30 | 20 | 55 |
| 11 | 6 | 0.1 × SSC | — | 1000 | 2 | 1–8 | — | 2 | 22 |
| 12 | 2 & 3 | EtOH/H$_2$O | 1:1 | 1000 | 2 | 1–8 | 60 | 2 | 22 |
| 13 | 2 & 3 | EtOH/H$_2$O | 7:3 | 1000 | 2 | 1–8 | 60 | 2 | 22 |
| 14 | 2 & 3 | EtOH/H$_2$O | 9:1 | 1000 | 2 | 1–8 | 60 | 2 | 22 |
| 15 | 2 | EtOH | — | 1000 | 2 | 1–8 | 60 | 2 | 22 |

I claim:

1. Apparatus for use in processing a sample on a support, the apparatus comprising a support; a sealing means; a support cell-forming member; clamping means pivotally mounted relative to the support cell-forming member; the support cell-forming member being clamped against the support by the clamping means with the sealing means positioned between the support and the support cell-forming member so as to effect a seal therebetween, and form a support cell comprising a substantially sealed chamber with a volume of 50–300 µl; the support cell-forming member being provided with a fluid inlet and a fluid outlet for the introduction and removal respectively of fluids used in processing the sample, whilst the chamber remains substantially sealed.

2. Apparatus according to claim 1, wherein the substantially sealed chamber has a volume of 50–150 µl.

3. Apparatus according to claim 1, wherein the fluid inlet enters the substantially sealed chamber in a channel or groove in the support cell-forming member which allows for even distribution of fluid across the width of the substantially sealed chamber.

4. Apparatus according to claim 1, wherein fluid flows into the fluid outlet via a channel or groove in the support cell-forming member which facilitates even egress of fluid across the width of the substantially sealed chamber.

5. Apparatus according to claim 1, wherein the support is a microscope slide.

6. Apparatus according to claim 1, wherein the sealing means comprises a gasket of silicone rubber or similar material.

7. Apparatus according to claim 1, comprising spring biasing means serving to bias the support cell-forming member against the support.

8. Apparatus according to claim 7, wherein the spring-biasing means comprises two spring-biasing members, each of said members acting on a respective opposed end region of the support cell-forming member.

9. Apparatus according to claim 1, further comprising temperature regulation means to regulate the temperature of the sample.

10. Apparatus according to claim 1, wherein the support cell-forming member comprises means for observing the presence of processing fluid within the support cell and thus monitoring the sample processing.

11. Apparatus according to claim 1, comprising a plurality of support cell-forming members.

12. Apparatus according to claim 1 comprising automating computer control means; the apparatus additionally comprising a plurality of support cell-forming members, fluid deliver means for deliver of processing fluid to the fluid inlet of each support cell-forming member and waste fluid collecting means for collecting fluid from the fluid outlet of each support cell-forming member.

13. Apparatus according to claim 12, wherein the fluid delivery means comprises one or more syringe pumps.

14. Apparatus according to claim 12 or 13, wherein each support cell-forming member is provided with an individual inlet valve close to a fluid inlet.

15. Apparatus according to claim 12, wherein each support cell is associated with a Peltier device to enable altering the temperature of the support cell.

16. Apparatus according to claim 12, wherein means is provided for the introduction of a processing fluid into the support cell via an alternative fluid delivery route.

17. Apparatus according to claim 16, wherein the fluid delivery means comprises two pumps, each pump being connected to a respective multi-inlet valve, thereby allowing a plurality of reservoirs of processing fluid to be connected to a single pump.

18. Apparatus according to claim 12, comprising temperature control means.

19. Apparatus according to claim 1, wherein the support cell-forming member is thermally insulated by an air-filled space between the said member and the apparatus.

20. In a method of processing a sample on a support, the improvement wherein the support comprises the apparatus of claim 1 or claim 12.

* * * * *